United States Patent [19]

Hasse et al.

[11] Patent Number: 5,246,433
[45] Date of Patent: Sep. 21, 1993

[54] ELASTICIZED DISPOSABLE TRAINING PANT AND METHOD OF MAKING THE SAME

[75] Inventors: Margaret H. Hasse, Wyoming; Russell P. Bridges, Cincinnati; Steven W. Miller, West Chester, all of Ohio

[73] Assignee: The Procter & Gamble Company, Cincinnati, Ohio

[21] Appl. No.: 795,560

[22] Filed: Nov. 21, 1991

[51] Int. Cl.$^5$ .............................................. A61F 13/15
[52] U.S. Cl. .............................. 604/396; 604/385.1; 604/385.2; 604/358
[58] Field of Search ............... 604/385.1, 385.2, 389, 604/378, 358, 396; 2/243 R, 243 B

[56] References Cited

U.S. PATENT DOCUMENTS

| | | |
|---|---|---|
| 3,237,625 | 3/1966 | Johnson . |
| 3,378,429 | 4/1968 | Obeda . |
| 3,457,132 | 7/1969 | Tuma et al. . |
| 3,526,554 | 9/1970 | Obeda . |
| 3,562,041 | 2/1971 | Robertson . |
| 3,657,033 | 4/1972 | Sager . |
| 3,679,526 | 7/1972 | Horton . |
| 3,733,238 | 5/1973 | Long et al. . |
| 3,737,361 | 6/1973 | Obeda . |
| 3,764,442 | 10/1973 | Parry . |
| 3,852,144 | 12/1974 | Parry . |
| 3,973,066 | 8/1976 | Smith, II et al. . |
| 4,205,679 | 6/1980 | Repke et al. . |
| 4,227,959 | 10/1980 | Brown . |
| 4,355,425 | 10/1982 | Jones et al. . |
| 4,381,781 | 5/1983 | Sciaraffa et al. . |
| 4,430,148 | 2/1984 | Schaefer . |
| 4,490,199 | 12/1984 | Dunning . |
| 4,491,491 | 1/1985 | Stumpf . |
| 4,500,372 | 2/1985 | Mion . |
| 4,515,595 | 5/1985 | Kievit et al. . |
| 4,560,427 | 12/1985 | Flood . |
| 4,610,678 | 9/1986 | Weisman et al. . |
| 4,610,680 | 9/1986 | LaFleur . |
| 4,610,681 | 9/1986 | Strohbeen et al. . |
| 4,619,649 | 10/1986 | Roberts . |
| 4,641,381 | 2/1987 | Heran et al. . |
| 4,646,362 | 3/1987 | Heran et al. . |
| 4,650,530 | 3/1987 | Mahoney et al. . |
| 4,673,402 | 6/1987 | Weisman . |
| 4,690,681 | 9/1987 | Haunschild et al. . |
| 4,693,771 | 9/1987 | Payet et al. . |
| 4,743,239 | 5/1988 | Cole . |
| 4,743,241 | 5/1988 | Igave et al. . |
| 4,747,846 | 5/1988 | Bolan et al. . |
| 4,834,735 | 5/1989 | Alemany et al. . |
| 4,857,067 | 8/1989 | Wood et al. . |
| 4,909,804 | 3/1990 | Douglas, Sr. . |
| 4,938,753 | 7/1990 | Van Gompel et al. . |
| 4,938,757 | 7/1990 | Van Gompel et al. . |
| 4,940,464 | 7/1990 | Van Gompel et al. . |
| 4,944,733 | 7/1990 | Casale . |
| 4,960,414 | 10/1990 | Meyer . |
| 4,968,313 | 11/1990 | Sabee . |

FOREIGN PATENT DOCUMENTS

| | | |
|---|---|---|
| 417766A1 | 3/1991 | European Pat. Off. . |
| 0460467A1 | 12/1991 | European Pat. Off. . |
| WO90/08524 | 8/1990 | PCT Int'l Appl. . |
| WO91/15364 | 10/1991 | PCT Int'l Appl. . |

Primary Examiner—Randall L. Green
Assistant Examiner—Rob Clarke
Attorney, Agent, or Firm—Stephen P. Kearney; Steven W. Miller; Monte D. Witte

[57] ABSTRACT

A unitary disposable garment, such as disposable training pants, having a high degree of stretch in the cross-machine direction and fitting a broad range of wearer sizes. The unitary disposable garment is manufactured from a chassis and has a waist opening, two leg openings and a pair of side seams which join the front portion of the chassis to the rear portion of the chassis. The unitary disposable garment preferably has an absorbent assembly, i.e. an absorbent insert, secured to the inner layer of the chassis. The chassis from which the unitary disposable garment is manufactured, has four elasticized ear flaps; each ear flap is elasticized by securing an elastomeric element thereto and mechanically stretching the ear flap and the elastomeric element such that the ear flap is elastically extensible in the direction of initial stretching. The front portion of the chassis is then joined to the rear portion of the chassis on each side of the disposable garment by a seam.

13 Claims, 14 Drawing Sheets

ELASTICIZED DISPOSABLE TRAINING PANT AND METHOD OF MAKING THE SAME

FIELD OF THE INVENTION

The present invention relates to disposable garments having fixed sides, which are placed in position on the wearer by inserting the wearer's legs into the leg openings and sliding the disposable garment into position about the wearer's lower torso. Examples of such disposable garments would include disposable underwear for children (e.g., toddlers) or adults, and disposable panties which may be used with catamenial devices such as tampons or sanitary napkins. The present invention relates more particularly to disposable absorbent articles such as training pants, incontinent garments (panties or briefs), and the like, having elasticized ear flaps.

BACKGROUND OF THE INVENTION

Infants and other incontinent individuals wear disposable absorbent articles to receive and contain urine and other bodily exudates. Absorbent articles having fixed sides, e.g. disposable training pants, have been popular for use on toilet-training children. Currently, training pants must be manufactured in several different sizes to accommodate the different size children of toilet-training age. Accordingly, to adequately meet the consumers needs, a manufacturer of disposable training pants must have several different sets of manufacturing equipment to produce the various sizes. It is, therefore, very desirable to have a design that would allow the manufacturer to make a one-size-fits-all training pant which will substantially meet the consumers needs by fitting a very broad range of child sizes. This requires that the training pant fit snugly about the waist and legs of smaller children without drooping, sagging or sliding down from its position about the lower torso, and must fit larger children without causing irritation to the skin about the waist, legs and crotch. Therefore, the disposable training pants must be elastically extensible about the waist and legs of the wearer, and the elastic elements must have a high degree of stretch.

Prior training pants have been made elastically extensible using elastic elements disposed in the training pants such that the waist opening and leg openings are at least partially encircled with elasticized bands. This method of using elastic elements is shown in U.S. Pat. Nos. 4,205,679 to Repke, et al.; U.S. Pat. No. 4,610,680 to LaFleur; U.S. Pat. No. 4,610,681 to Strohbeen, et al.; U.S. Pat. No. 4,641,381 to Heran, et al.; U.S. Pat. No. 4,909,804 to Douglas, Sr.; and U.S. Pat. No. 4,960,414 to Meyer. Although training pants made according to these methods will allow the absorbent articles to fit slight variations in waist size and slight variations in leg size, training pants made according to these particular methods are limited in their range of fit sizes because the elastic elements do not have a high degree of stretch, and because the fixed sides are not elastically extensible.

Another method of elasticizing disposable training pants is shown in U.S. Pat. Nos. 4,490,464; 4,938,753; and 4,938,757 all of which issued to Van Gompel, et al. These patents disclose a pant-like garment formed by attaching discrete stretchable members to the side edges of the main body of the garment. Although training pants made according to this method will also allow the absorbent articles to fit slight variations in size, a training pant made according to this particular method is limited in its range of fit sizes because the fixed sides are formed by securing discrete stretchable members to the side edges of the main body of the garment which results in nonfunctional attachment zones, i.e. the area where the main body and the discrete stretchable members overlap forms an area that is not elongatable and is not absorbent. A training pant made according to this particular method is also limited in its range of fit sizes because the discrete stretchable members which make up the side panels of the garment do not have a high degree of stretch.

It is, therefore, an object of the present invention to provide a method of making an elasticized disposable garment with a high degree of stretch such that the disposable garment will comfortably fit wearers in a broad range of sizes.

SUMMARY OF THE INVENTION

According to the present invention, a method of making a disposable garment having at least two, and preferably four, elasticized ear flaps, is provided. The method includes providing a chassis comprising elongatable, ear flaps having an elastomeric member secured thereto to form a laminate; and mechanically stretching the laminate so that the ear flap is permanently elongated and the laminate is elastically extensible in the direction of initial stretching, once the initial stretching forces are removed from the laminate.

While the disposable garment of the present invention may take many forms, it preferably comprises a chassis having an elasticized waist opening, elasticized leg openings, elasticized ear flaps, an absorbent assembly comprising a backsheet, topsheet, and absorbent core, and at least one flangeless seam comprising a mass of fused polymeric material which extends from the garment about 1/16" or less, preferably extends from the garment about 1/32" or less, and in a preferred embodiment, forms a splice between the front and rear portions of the disposable garment.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which like designations are used to designate substantially identical elements, and in which:

FIG. 8B is a highly enlarged view taken at the inset 8B shown in FIG. 8 showing the degree of meshing of the corrugated rolls with one another as the "zero strain" stretch laminate portion of the chassis web passes there between;

DETAILED DESCRIPTION OF THE INVENTION

The elasticized ear flaps of the present invention are described as being used on particular embodiments of a disposable training pant. However, it should be understood that the present invention is intended for use on other training pant designs, as well as on other types of disposable garments.

Figure 1:
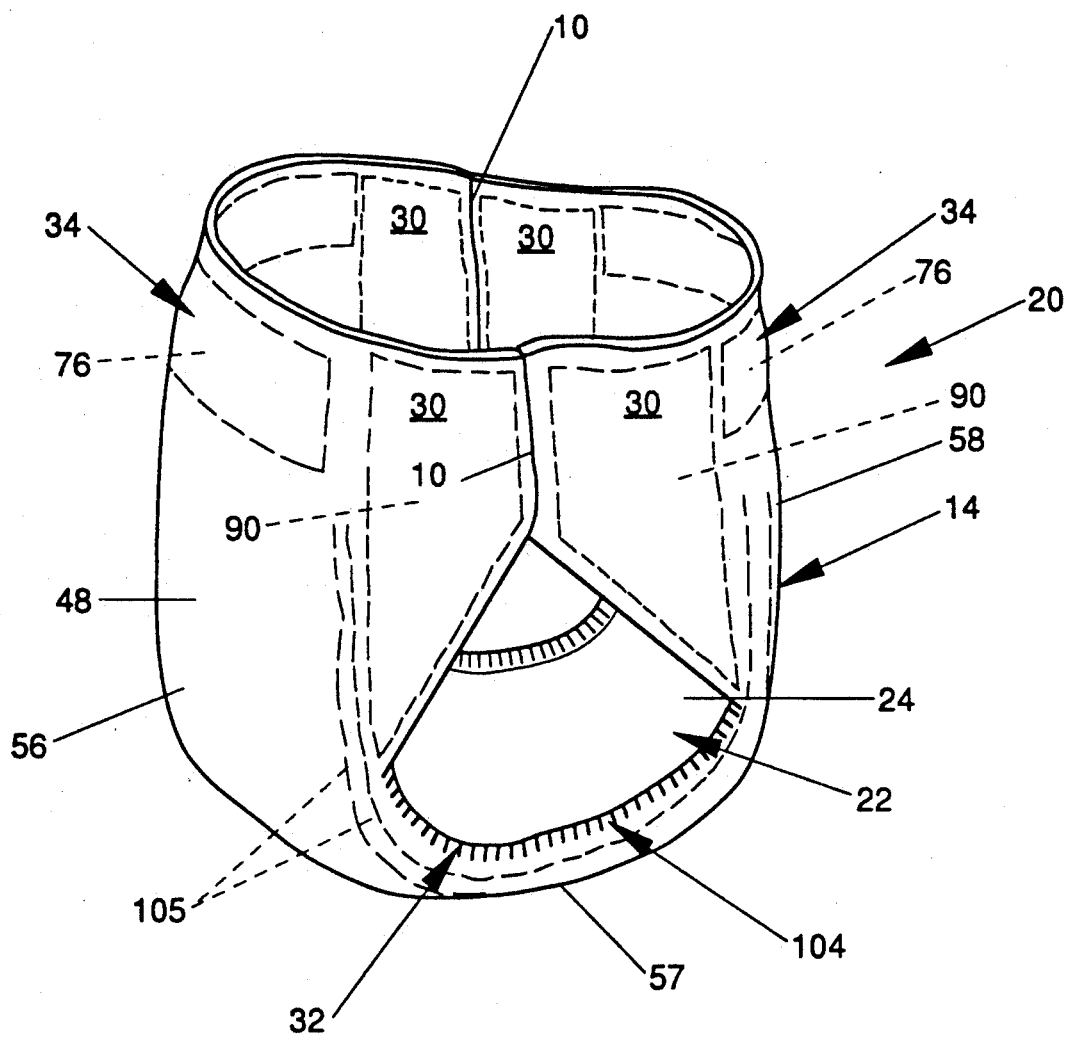
FIG. 1 is a perspective view of the disposal training pant embodiment of the present invention in a typical in-use configuration as it would be applied to a wearer.

A unitary disposable garment is one which is intended to be discarded after it is used (i.e., it is not intended to be laundered or otherwise restored or reused), and which does not require separately manipulative parts such as a separate chassis and separate ear flaps. The disposable garment may be provided with an absorbent assembly which is placed in close proximity to the body of the wearer to absorb and contain the various exudates discharged from the body. A preferred embodiment of the unitary disposable garment of the present invention, disposable training pants 20, is shown in FIG. 1. The training pants 20 of FIG. 1, comprise a chassis 14, side seams 10, and an absorbent assembly 22.

Figure 2:
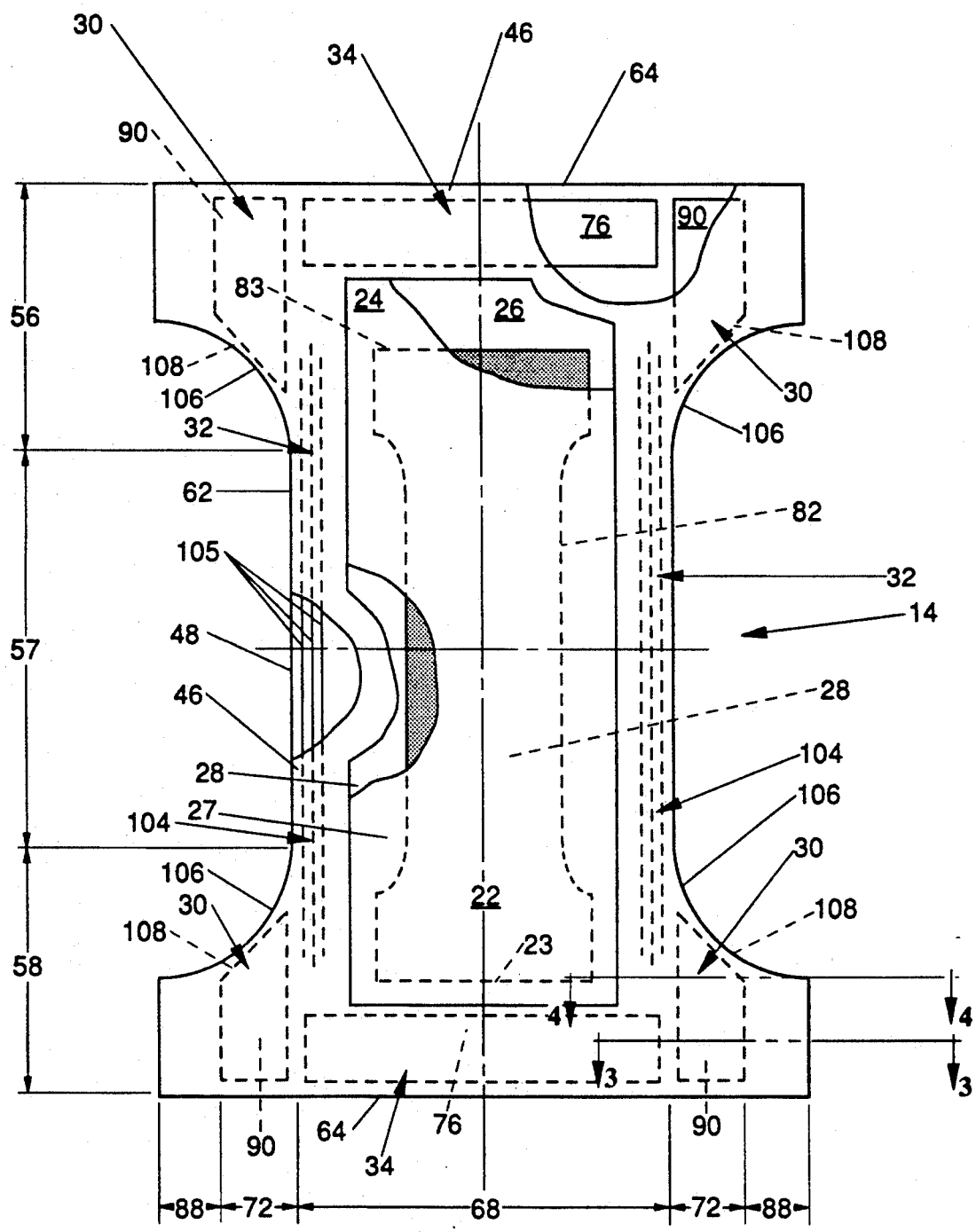
FIG. 2 is a plan view of the chassis of the training pant embodiment of the present invention having portions cut away to reveal the underlying structure, the surface which will form the outer surface of the disposable garment facing away from the viewer.
Figure 3:
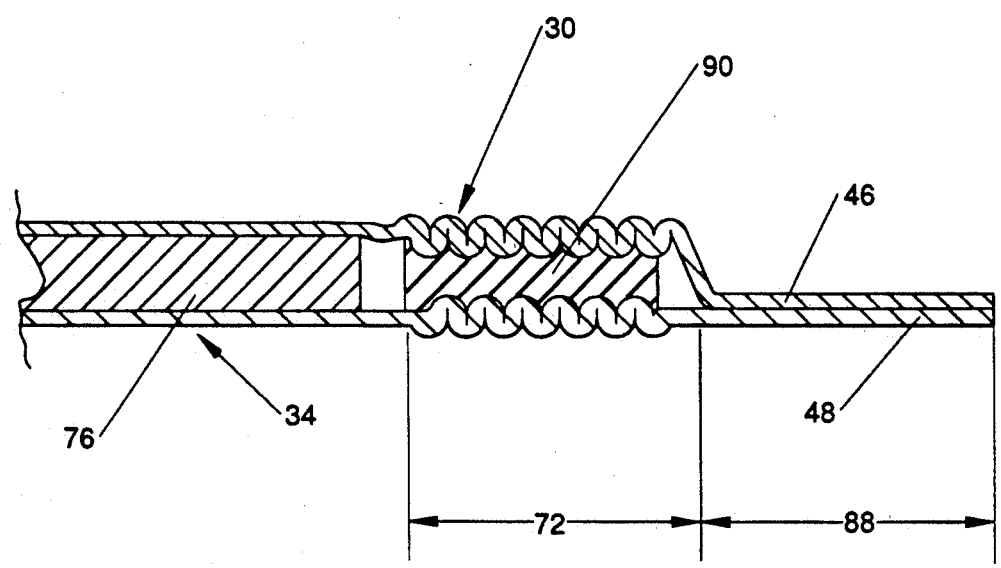
FIG. 3 is a fragmentary sectional view of the chassis shown in FIG. 2 taken along section line 3—3 of FIG. 2.

FIG. 2 is a partially cut-away perspective view of the disposable training pants 20 of FIG. 1, prior to the front portion 56 and the rear portion 58 of the chassis 14 being joined together by the seams 10. The chassis 14 of the present invention preferably has a symmetric, modified hour-glass shape. The chassis 14 will have at least a front portion 56, a rear portion 58, a crotch portion 57, longitudinal side regions 88, and ear flaps 72 and will comprise an elastic ear flap member 90 operatively associated with each ear flap 72 to form a laminated ear flap which will be elastically activated by a mechanical stretching process which will be described in greater detail herein below. The absorbent assembly 22 is secured to the chassis 14.

As shown in FIG. 2, a preferred embodiment of the chassis 14 further comprises an outer layer 48 and an inner layer 46 with the elastic ear flap members 90, elastic waistband members 76, and elastic strands 105 preferably secured between the inner layer 46 and outer layer 48.

The outer layer 48 is that portion of the chassis 14 which will form the exterior of the disposable training pants 20, i.e. face away from the wearer. The outer layer 48 is compliant, soft feeling, and non-irritating to the wearer's skin. A suitable outer layer may be manufactured from a wide range of materials, such as plastic films; or woven or non-woven webs of natural fibers (e.g. wood or cotton fibers), synthetic fibers (e.g. polyester or polypropylene fibers), or a combination of natural and synthetic fibers. Preferably, the outer layer 48 is hydrophobic and is made of a material containing a significant amount of thermoplastic fibers, typically 50% or more, preferably 100%. Preferably the outer layer is a carded nonwoven web of polypropylene fibers. A suitable outer layer is Series 6700 Nonwovens manufactured by Scott Nonwovens of Landisville, N.J.

The inner layer 46 is that portion of the chassis 14 which will form the interior of the chassis 14, and will contact at least the waist and legs of the wearer. The inner layer is also compliant, soft feeling, and non-irritating to the wearer's skin. A suitable inner layer 46 may be manufactured from a wide range of materials, such as plastic films; or woven or non-woven webs of natural fibers (e.g. wood or cotton fibers), synthetic fibers (e.g. polyester or polypropylene fibers), or a combination of natural and synthetic fibers. Preferably the inner layer 46 is made of a material containing a significant amount of thermoplastic fibers, typically 50% or more, preferably 100%. Preferably the inner layer is also a carded nonwoven web of polypropylene fibers. More preferably, the inner layer 46 is made of the same material as the outer layer 48. A suitable inner layer is Series 6700 Nonwovens manufactured by Scott Nonwovens of Landisville, N.J.

The inner layer 46 is preferably positioned adjacent to the outer layer 48 and is preferably Joined thereto by attachment means (not shown) such as those well known in the art. For example, the inner layer 46 may be secured to the outer layer 48 by a uniform continuous layer of adhesive, a patterned layer of adhesive, or an array of separate lines, spirals, or spots of adhesive. Adhesives which have been found to be satisfactory are manufactured by Findley Adhesives of Elm Grove, Wisc. and marketed as Findley 2031. Alternatively, the attachment means may comprise heat bonds, pressure bonds, ultrasonic bonds, dynamic mechanical bonds, or any other suitable attachment means or combinations of these attachment means as are known in the art. As used herein, the term "joined" encompasses configurations whereby an element is directly secured to the other element by affixing the element directly to the other element, and configurations whereby the element is indirectly secured to the other element by affixing the element to intermediate member(s) which in turn are affixed to the other element. In a preferred embodiment of the present invention, the inner layer 46 and the outer layer 48 are indirectly joined together by directly Joining them to the elastic ear flap members 90, elastic waistband members 76, and elastic strands 105 and are joined directly to each other in the areas extending beyond the elastic ear flap members 90, elastic waistband members 76, and elastic strands 105.

In a preferred embodiment of the present invention, at least a portion of the chassis inner and outer layers 46, 48 will be subjected to mechanical stretching in order to provide a "zero strain" stretch laminate that forms the elasticized ear flaps 30. Thus, the inner and outer layers 46, 48 are preferably elongatable, most preferably drawable, but not necessarily elastomeric, so that the inner and outer layers 46, 48 will, upon mechanical stretching, be at least to a degree permanently elongated such that they will not fully return to their original undistorted configuration. In preferred embodiments, the inner and outer layers 46, 48 can be subjected to mechanical stretching without undue rupturing or tearing. Thus, it is preferred that the inner and outer layers 46, have a low cross-machine direction (lateral direction) yield strength.

The chassis 14 of the disposable training pants 20 preferably further comprises elasticized leg cuffs 32 for providing improved containment of liquids and other body exudates. Each elasticized leg cuff 32 may comprise several different embodiments for reducing the leakage of body exudates in the leg regions. (The leg cuff can be and is sometimes also referred to as leg bands, side flaps, barrier cuffs, or elastic cuffs.) U.S. Pat. No. 3,860,003 entitled "Contractable Side Portions For a Disposable Diaper" issued to Buell on Jan. 14, 1975, describes a disposable diaper which provides a contractible leg opening having a side flap and one or more elastic members to provide an elasticized leg cuff (gasketing cuff). U.S. Pat. No. 4,909,803 entitled "Disposable Absorbent Article Having Elasticized Flaps" issued to Aziz and Blaney on Mar. 20, 1990, describes a disposable diaper having "stand-up" elasticized flaps (barrier cuffs) to improve the containment of the leg regions. U.S. Pat. No. 4,695,278 entitled "Absorbent Article Having Dual Cuffs" issued to Lawson on Sep. 22, 1987, describes a disposable diaper having dual cuffs including a gasketing cuff and a barrier cuff. U.S. Pat. No. 4,704,115 entitled "Disposable Waist Containment Garment" issued to Buell on Nov. 3, 1987, discloses a disposable diaper or incontinent garment having side-edge-leakage-guard gutters configured to contain free liquids within the garment. Each of these patents are incorporated herein by reference. While each elasticized leg cuff 32 may be configured so as to be similar to any of the leg bands, side flaps, barrier cuffs, or elastic cuffs described above, it is preferred that each elasticized leg cuff 32 comprise at least a side flap 104 and one or more elastic strands 105.

The chassis 14 of the disposable training pants 20 further preferably comprises an elasticized waistband 34 disposed adjacent the end edge 64 of the disposable training pants 20 in at least the rear portion 58, and more preferably has an elasticized waistband 34 disposed in both the front portion 56 and the rear portion 58. The waistband of the disposable training pants 20 is that portion which is intended to be placed adjacent the wearer's waist. The elasticized waistband 34 provides a member that maintains a defined area coverage, contacts the wearer's waist, and is elastically extensible in at least the lateral direction so as to dynamically fit against the waist of the wearer and to dynamically conform to the waist of the wearer so as to provide improved fit. Thus, the waistband is generally that portion of the disposable training pants 20 extending from the end edge 64 of the disposable training pants 20 to at least the waist edge 83 of the absorbent core 28. While the elasticized waistband 34 can comprise a separate element affixed to the chassis 14 of the disposable training pants 20, the waistband is preferably an extension of other elements of the disposable training pants 20 such as the inner layer 46, the outer layer 48, or any combination of these elements and an elastomeric material joined thereto. Alternatively, the topsheet 24 and the backsheet 26 of the absorbent assembly 22, may extend beyond the edges of the absorbent core 28 and have an elastomeric material joined thereto to form an elasticized waistband. Disposable training-pants are often constructed so as to have two elasticized waistbands; one positioned in the front portion 56 and one positioned in the rear portion 58. The disposable training pants 20 at least has an elasticized waistband 34 disposed in at least the central region 68 of the rear portion 58. Preferably, as shown in FIG. 2, another elasticized waistband is disposed in the front portion 56. Preferably both elasticized waistbands 34 are disposed between the elasticized ear flaps 30.

The elasticized waistband 34 may be constructed in a number of different configurations including those described herein with regard to the elasticized side panels. In a preferred embodiment of the present invention shown in FIG. 2, the elasticized waistband 34 comprises an elastic waistband member 76 interposed between the inner cover 46 and the outer cover 48 and operatively associated with either or both the inner cover 46 and the outer cover 48 to gather the front portion 56 and rear portion 58 of the disposable training pants 20. An example of such an elasticized waistband for use herein is the elasticized waistband disclosed in U.S. Pat. No. 4,515,595 entitled "Disposable Diapers With Elastically Contractible Waistbands", which issued to Kievit and Osterhage on May 7, 1985, and which patent is incorporated herein by reference.

Any suitable elastomeric material as known in the art may be used as the elastic waistband member 76 of the present invention. Examples of suitable elastomeric materials include elastomeric films, elastomeric foams such as polyurethane foams or crosslinked natural rubber foams; formed elastic scrim; elastomeric films such as heat shrinkable elastic materials; elastomeric film laminates such as a laminate of a heat-shrinkable elastomeric film and a resilient member; elastomeric stretch laminates such as "zero strain" stretch laminates as described hereinafter or mechanically stretched pretensioned stretch laminates; and elastic strands made from rubber, LYCRA, or other materials. In a preferred embodiment, the elastic waistband member 76 comprises a heat shrinkable elastomeric film.

In an alternative embodiment, the elasticized waistbands 34 and the elasticized ear flaps 30 can be formed by securing a single piece of elastomeric material to the disposable garment 20 in both the ear flaps 72 and the central region 68 of the rear portion 58 and securing a single piece of elastomeric material to the disposable garment 20 in both the ear flaps 72 and central region 68 of the front portion 56. Thus, the elasticized waistband 34 and the elasticized ear flaps 30 can be formed from the same piece of material to form a unitary structure.

In a preferred embodiment, the chassis 14 comprises elasticized ear flaps 30 in the front portion 56 and the rear portion 58. The elasticized ear flaps 30 are unitary elements of the chassis, i.e. they are not separately manipulative elements secured to the chassis, but rather are formed from and are extensions of the chassis materials. The elasticized ear flaps 30 provide an elastically extensible feature that provides a more comfortable and contouring fit by initially conformably fitting the disposable garment to the wearer and sustaining this fit throughout the time of wear well past when the disposable garment has been loaded with exudates since the elasticized ear flaps allow the sides of the disposable garment to expand and contract.

As shown in FIG. 2, each ear flap 72 comprises that portion of the chassis 14 that extends laterally outwardly from and along the central region 68 of the chassis 14 to the longitudinal side region 88 of the chassis 14. The ear flap 72 generally extends longitudinally from the end edge 64 of the chassis 14 to the portions of the longitudinal edge 62 of the chassis 14 that forms the leg opening (this segment of the longitudinal edge 62 being designated as leg edge 106). In a preferred embodiment of the present invention, each ear flap is formed by the portions of the inner layer 46 and the outer layer 48 that extend beyond the central region 68 of the chassis 14.

In a preferred embodiment of the present invention, the elastic ear flap members 90 are operatively associated with the chassis 14 in the ear flaps 72, preferably between the inner layer 46 and the outer layer 48, so that the elastic ear flap members 90 allow the elasticized ear flaps 30 to be elastically extensible in the lateral direction (laterally elastically extensible). As used herein, the term "elastically extensible" means a segment or portion of the chassis that will elongate in at least one direction (preferably the lateral direction for the ear flaps and the waistbands) when tensional forces (typically lateral tensional forces for the ear flaps and the waistbands) are applied, and will return to about its previous size and configuration when the tensional forces are removed. Generally, elastomeric materials useful in the present invention will contractively return to at least about 75% of their original configuration within about 5 seconds or less upon stretch and immediate release thereof (i.e., a "snappy" elastic).

In an especially preferred embodiment, the elastic ear flap member 90 is operatively associated in the ear flap 72 by joining the elastic ear flap member 90 to the inner layer 46, outer layer 48, or both while the elastic ear flap member 90 is in a substantially untensioned condition. At least a portion of the resultant composite elastomeric laminate containing the elastic ear flap member 90 is then subjected to mechanical stretching sufficient to permanently elongate the inner layer and the outer layer components (nonelastic components) of the laminate. The composite elastomeric laminate is then allowed to return to its substantially untensioned condition. The elasticized ear flap is thus formed into a "zero strain" stretch laminate. (Alternatively, the elastic ear flap member could be operatively associated in a tensioned condition and then subjected to mechanical stretching; although this is not as preferred as a "zero strain" stretch laminate.) As used herein, the term "zero strain" stretch laminate refers to a laminate comprised of at least two plies of material which are secured to one another along at least a portion of their coextensive surfaces while in a substantially untensioned ("zero strain") condition; one of the plies comprising a material which is stretchable and elastomeric (i.e., it will return substantially to its untensioned dimensions after an applied tensile force has been released) and a second ply which is elongatable (but not necessarily elastomeric) so that upon stretching the second ply will be, at least to a degree, permanently elongated so that upon release of the applied tensile forces, it will not fully return to its original undeformed configuration. The resulting "zero strain" stretch laminate is thereby rendered elastically extensible, at least up to the point of initial stretching, in the direction of initial stretching. Examples of such "zero strain" stretch laminates are disclosed in U.S. Pat. No. 2,075,189 issued to Galligan, et al. on Mar. 30, 1937; U.S. Pat. No. 3,025,199 issued to Harwood on Mar. 13, 1962; U.S. Pat. No. 4,107,364 issued to Sisson on Aug. 15, 1978; U.S. Pat. No. 4,209,563 issued to Sisson on Jun. 24, 1980; and U.S. Pat. No. 4,834,741 issued to Sabee on May 30, 1989. Each of these patents are incorporated herein by reference.

Particularly preferred methods and apparatus used for making "zero strain" stretch laminates out of the inner layer, outer layer, and an elastomeric member positioned between the same, use meshing corrugated rolls to mechanically stretch the components. A discussion of suitable apparatus and methods for mechanically stretching portions of a diaper is contained in the hereinbefore referenced U.S. Pat. No. 4,107,364 issued to Sisson on Aug. 15, 1978 and U.S. Pat. No. 4,834,741 issued to Sabee on May 30, 1989. Particularly preferred apparatus and methods are disclosed in co-pending, commonly assigned, U.S. patent application Ser. No. 07/662,536 entitled "Improved Method And Apparatus For Incrementally Stretching A Zero Strain Stretch Laminate Web To Impart Elasticity Thereto"; P&G Case 4339; filed by Gerald M. Weber et al. on Feb. 28, 1991; U.S. patent application Ser. No. 07/662,537 entitled "Improved Method And Apparatus For Incrementally Stretching Zero Strain Stretch Laminate Web In A Non-Uniform Manner To Impart A Varying Degree of Elasticity Thereto"; P&G Case 4340; filed by Kenneth B. Buell et al. on Feb. 28, 1991; and U.S. patent application Ser. No. 07/662,543 entitled "Improved Method And Apparatus For Sequentially Stretching Zero Strain Stretch Laminate Web To Impart Elasticity Thereto Without Rupturing The Web"; P&G Case 4341; filed by Gerald M. Weber et al. on Feb. 28, 1991; the specifications and drawings of which each are incorporated herein by reference.

Figure 8:
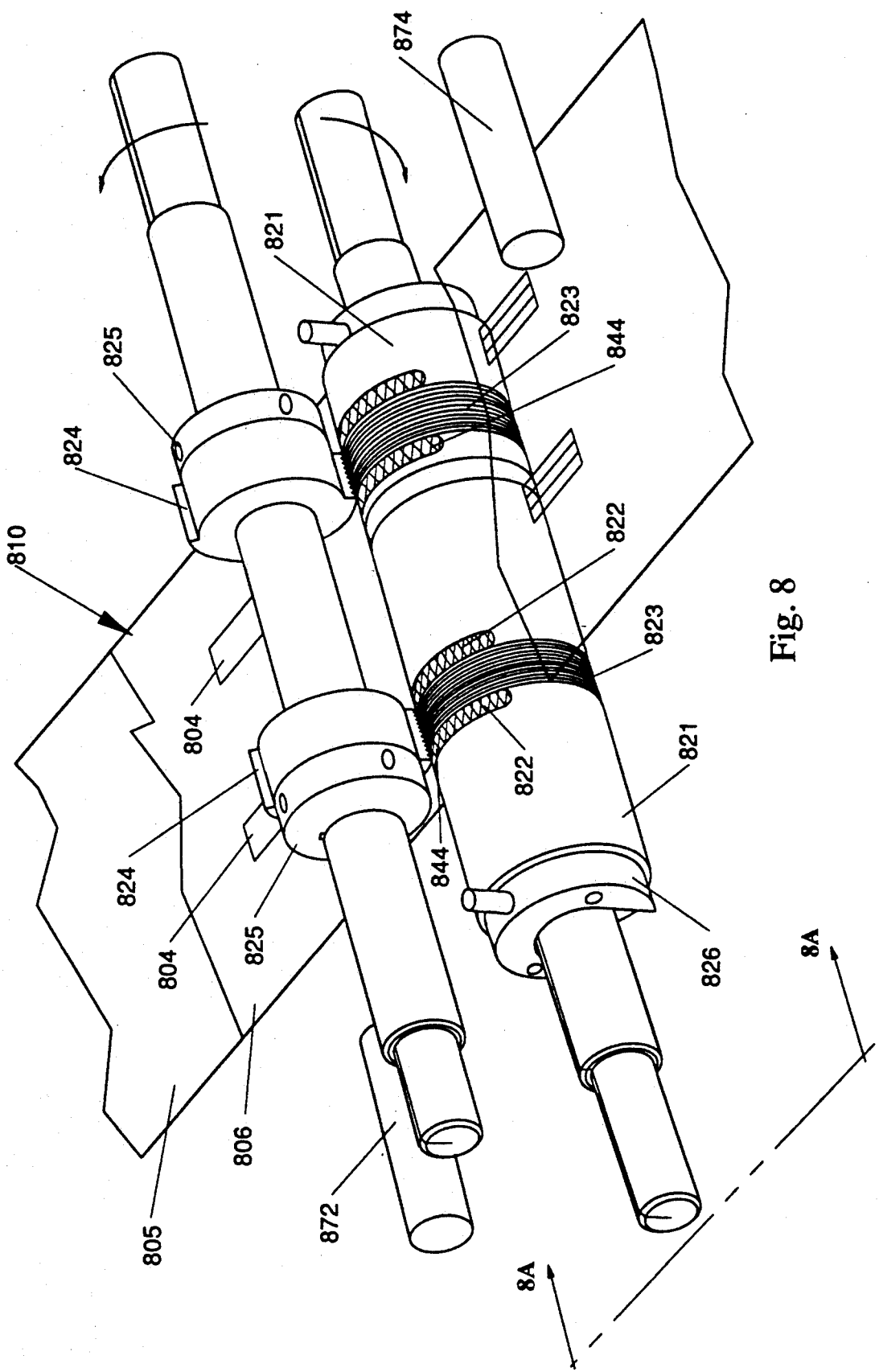
FIG. 8 is a simplified perspective view of an apparatus that employs a vacuum web restraint system for mechanically stretching a portion of a chassis web using meshing corrugated rolls

Details of a particularly preferred incremental stretching system which can be employed in making "zero strain" stretch laminate elasticized ear flaps of the present invention are set forth in FIG. 8. The fully assembled chassis web 810 including the "zero strain" ear flap web is directed through the incremental stretching system.

Referring to FIG. 8, the timing of the chassis web 810 containing the substantially untensioned elastic ear flap members (elastomeric patches 804) is such that the substantially untensioned elastomeric patches 804 substantially coincide with the corrugated or grooved segments 824 contained on the uppermost corrugated rolls 825 as the chassis web 810 passes between the segments 824 of the uppermost corrugated rolls 825 and the continuously corrugated or grooved lowermost corrugated rolls 821.

While the exact configuration, spacing and depth of the complementary grooves on the uppermost and lowermost corrugated rolls will vary, depending upon such factors as the amount of elasticity desired in the "zero strain" stretch laminate portion, a peak-to-peak groove pitch of approximately 0.150 inches, an included angle of approximately 12 degrees as measured at the peak, and a peak-to-valley groove depth of approximately 0.300 inches have been employed in a particularly preferred embodiment of the present invention. The exterior peak of each corrugation on the aforementioned corrugated rolls typically exhibits a radius of approximately 0.010 inches, while the internal groove formed between adjacent corrugations typically exhibits a radius of approximately 0.040 inches. When the corrugated rolls are adjusted so that their opposing peaks overlap one another to a depth between about 0.150 and about 0.175 inches, good elastic characteristics have been produced in a laminate web of the present invention comprised of 35-50 mil thick elastomeric rubber foam patches substantially continuously bonded on their opposed surfaces to a nonwoven inner layer and a nonwoven outer layer having basis weights in the range of about 20 to 30 grams per square yard and comprised of polypropylene fibers.

The degree of overlap of the opposing peaks on the aforementioned corrugated rolls may of course be adjusted, as desired, to produce more or less extensibility in the resultant "zero strain" stretch laminate web. For the aforementioned roll geometry and laminate web construction, peak-to-peak overlap depths ranging from as little as about 0.050 inches to as much as about 0.225 inches are feasible.

Figure 8A:
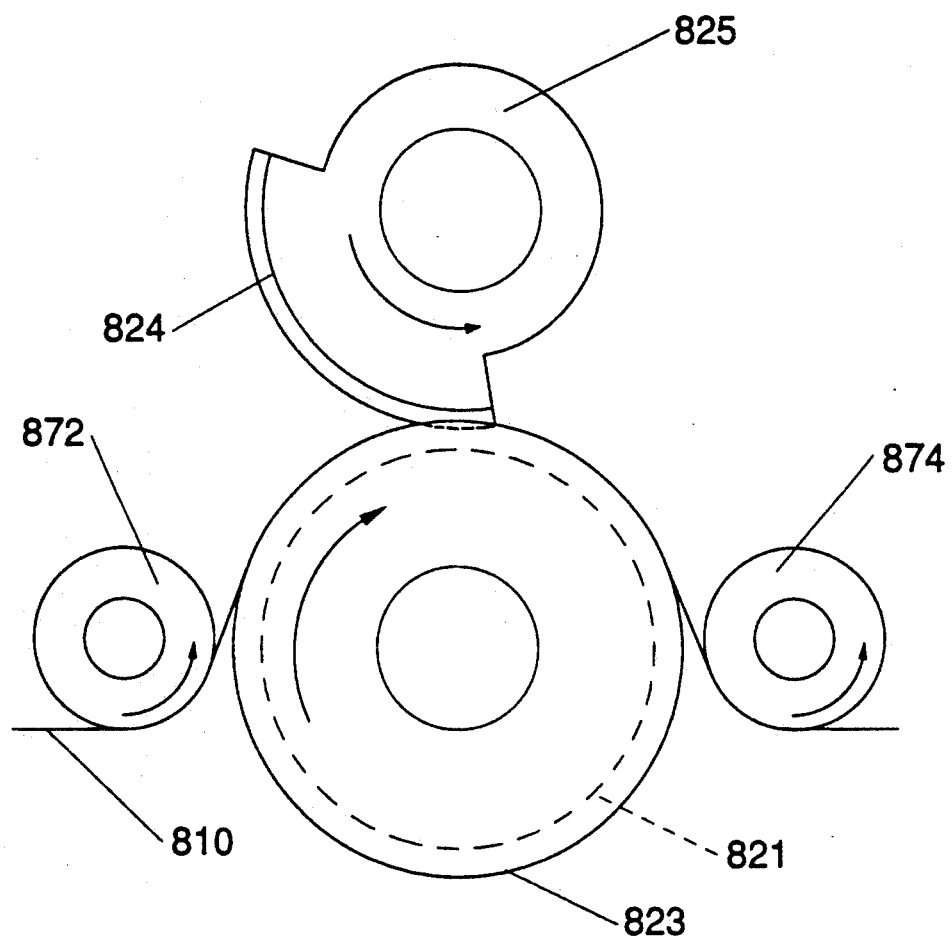
FIG. 8A is a simplified view taken along line 8A—8A in FIG. 8 showing the manner in which idler rolls are used to cause the chassis web to wrap the lower most corrugated rolls.

As can be seen from FIG. 8A, the chassis web 810 is caused by the idler rolls 872, 874 to wrap the lowermost corrugated rolls 821 sufficiently to cover the active vacuum ports 822 (shown in FIG. 8) located immediately adjacent each continuous set of grooves 823 on the lowermost rolls 821. The vacuum ports 822, which are positioned so as to substantially coincide with the grooved segments 824 on the uppermost corrugated rolls 825, are internally connected through the rolls 821 to a pair of vacuum manifolds 826 which exert suction against the chassis web 810 as the chassis web is acted upon by the grooved segments 824 of the uppermost corrugated rolls 825.

To minimize the build up of either the adhesive used to secure the untensioned elastomeric patches 804 to the inner layer web 805 and the outer layer web 806 or the adhesive used to secure the coinciding portions of the inner layer web and the outer layer web to one another, the grooved segments 824 on the uppermost rolls 825 and the continuous grooves 823 on the lowermost rolls 821 may be either comprised of a low friction material, such as TEFLON, or coated with a self-lubricating low friction material such as Permalon No. 503 spray coating, as available from Micro Surface Corporation of Morris, Ill.

The vacuum ports 822 on the lowermost rolls 821 are preferably covered by a porous material, such as 0.090 inch mesh honeycomb 844, to provide support to the portions of the chassis web 810 acted upon by the vacuum and to provide a good gripping surface against the web so as to substantially prevent lateral slippage or movement of the web across the honeycomb surface whenever the web is acted upon by the vacuum.

Under optimum circumstances, the maximum degree of incremental stretching which can be imparted to the "zero strain" portions of the ear flap containing the elastomeric patches 804 is determined by the depth of engagement between the grooves on segments 824 of the uppermost corrugated rolls 825 and the continuous grooves 823 on the lowermost corrugated rolls 821.

However, it has been discovered that unless the stretch laminate web is substantially prevented from slipping or contracting in a direction substantially parallel to the direction of web stretching as it passes between the meshing corrugated rolls, the optimum degree of incremental stretching is not realized. Therefore, in its most preferred form, the incremental web stretching operation is carried out while the outermost portions of all three layers comprising the "zero strain" stretch laminate are subjected to restraint, as generally shown in the cross-section of FIG. 8B, to substantially prevent the "zero strain" stretch laminate portions of the chassis web from slipping or contracting in a direction parallel to the desired direction of stretching as it passes between the sets of sequentially positioned meshing corrugated rolls.

However, the present invention may also, if desired, be practiced to advantage by restraining only the elongatable or drawable layer or layers of the composite, i.e., it is not an absolute requirement that the outermost portions of the elastomeric patches also be restrained during the incremental stretching operation. In the latter instance, the elongatable or drawable layer or layers are still permanently elongated during the incremental stretching process, but the z-direction bulking in the resultant "zero strain" stretch laminate web may be somewhat less pronounced when the stretching tension is removed. This is due to the fact that the elastomeric patch undergoes a lesser degree of initial stretching during such a process. Accordingly, it can only undergo this same amount of retraction when it returns to its undistorted configuration.

A "zero strain" stretch laminate embodiment of the aforementioned type may also exhibit some degree of disproportionate localized straining in the elongatable web or webs, particularly in the areas immediately adjacent the opposed edges of the elastomeric patches. In the case of an opaque polymeric inner layer web or outer layer web, these disproportionately strained portions can become sufficiently thinned that they may even appear transparent despite the fact that no rupture has taken place. In such instances the functionality, (e.g., the imperviousness) of the "zero strain" stretch laminate portions of the chassis web is not impaired. Embodiments of the latter type are normally employed in situations where the aesthetic appearance of the "zero strain" stretch laminate portions of the resultant disposable garment is either hidden from view by the design or configuration of the disposable garment or, if visible, is of no concern to the user of the disposable garment.

In still another embodiment of the present invention even rupture of one or more of the elongatable nonelastic webs may not render the resultant "zero strain" stretch laminate web unacceptable for its intended purpose (e.g., where a portion of the backsheet or topsheet of the absorbent assembly, makes up a component of the laminate web, rupture of the backsheet or topsheet does not necessarily destroy the laminate web's functionality for its intended purpose as long as one of the other plies in the laminate web provides the desired function in the finished article). For example, some degree of rupturing in the elongatable backsheet web will not destroy the imperviousness of the resultant chassis web if the elastomeric patches comprise a liquid-impervious material). This is particularly true with respect to those "zero strain" stretch laminate web embodiments employing substantially continuous bonding between the plies in question, since relatively close adherence of the plies to one another after incremental stretching renders such ply damage difficult to detect by the end use of the disposable garment.

Figure 8B:
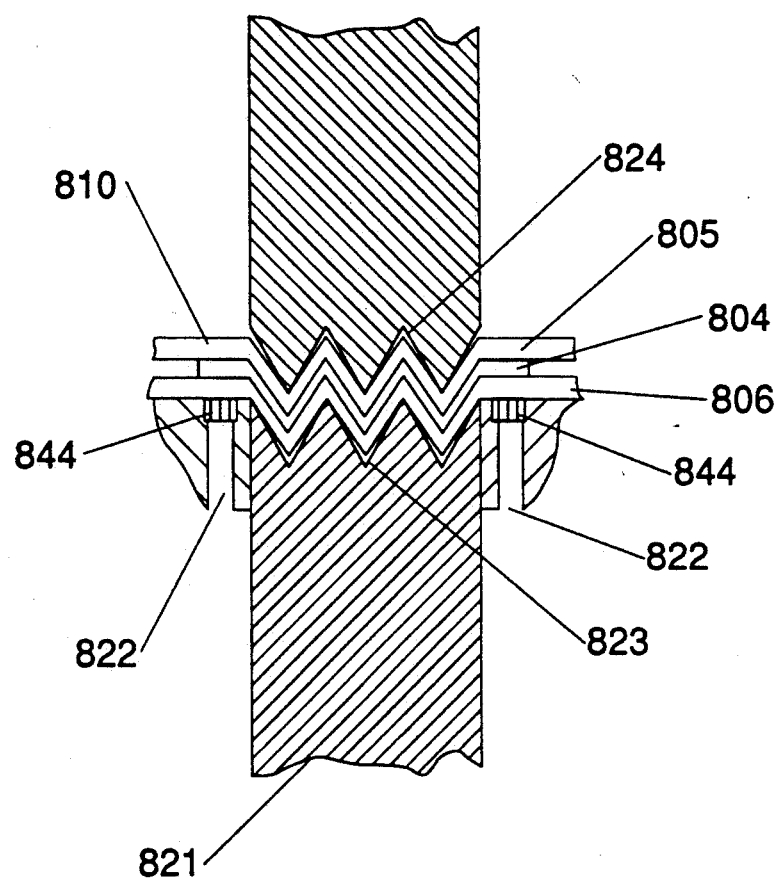

The suction forces applied to the chassis web 810 shown in FIGS. 8-8B by the vacuum ports 822 acting through the porous honeycomb material 844 substantially prevent those portions of the chassis web 810 containing the substantially untensioned elastomeric patches 804 from slipping or contracting in a laterally inward direction as they pass between the meshing portions of the continuous grooves 823 on the lowermost corrugated rolls 821 and the grooved segments 824 on the uppermost corrugated rolls 825.

Because the "zero strain" stretch laminate portions of the chassis web 810 containing the elastomeric patches 804 are laterally restrained throughout the sequential web stretching operation, all portions of the "zero strain" stretch laminate web located intermediate the points of restraint are subject to substantially uniform incremental stretching as the web passes between the continuous grooves 823 on the lowermost corrugated rolls 821 and the meshing portions of the grooved segments 824 on the uppermost corrugated rolls 825.

This not only maximizes the effectiveness of the incremental web stretching operation by forcing the elongatable inner cover and outer cover webs secured to the elastomeric patches to undergo the fullest possible degree of elongation during the stretching operation, but also substantially prevents disproportionately high straining of the inner layer and/or outer layer webs to which they are secured in the areas immediately adjacent the opposed peripheral edge portions of the elastomeric patches.

Figure 9:
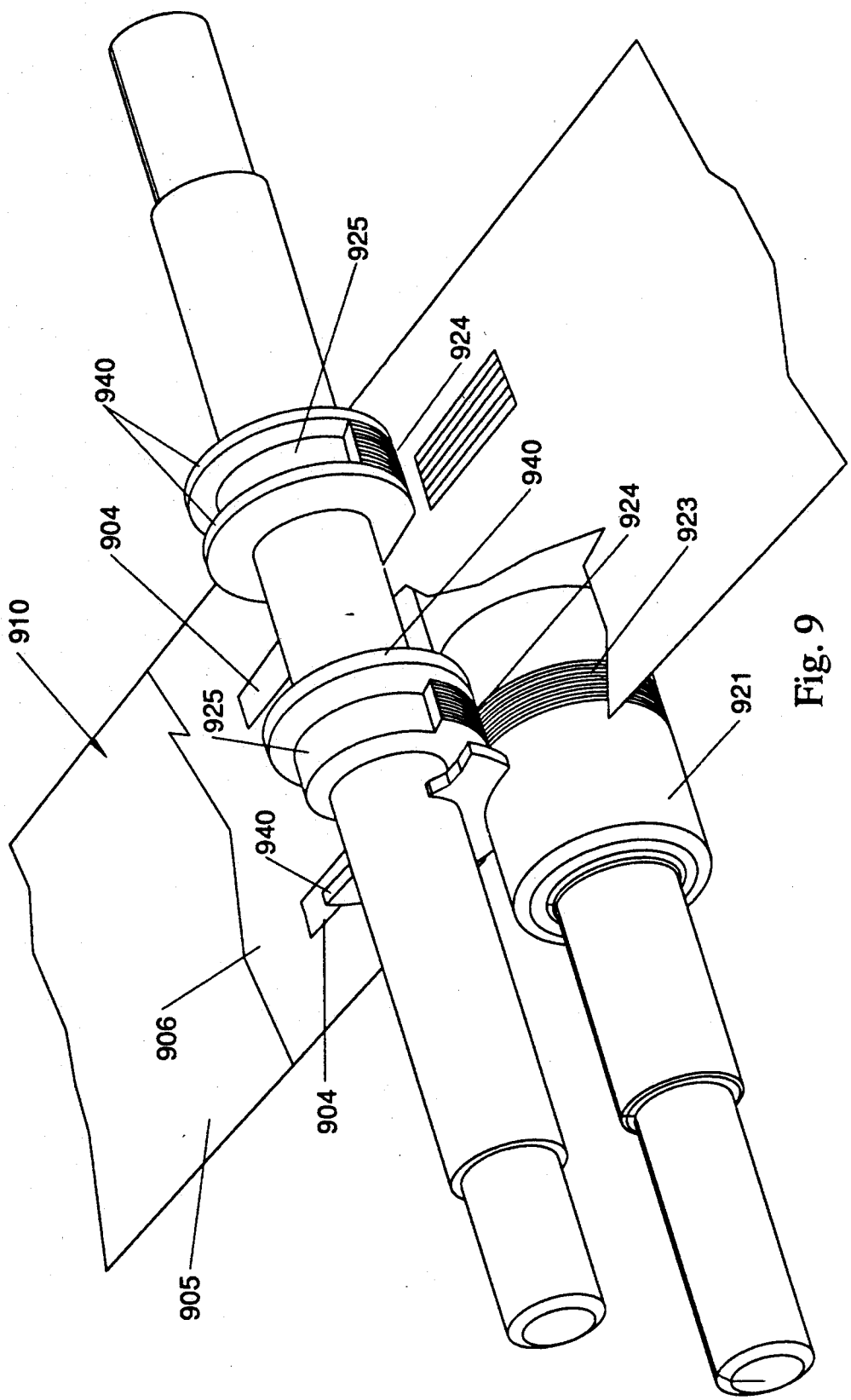
FIG. 9 is a simplified perspective view showing an alternative web restraint system of the present invention which may be used during the incremental stretching process disclosed herein.
Figure 9A:
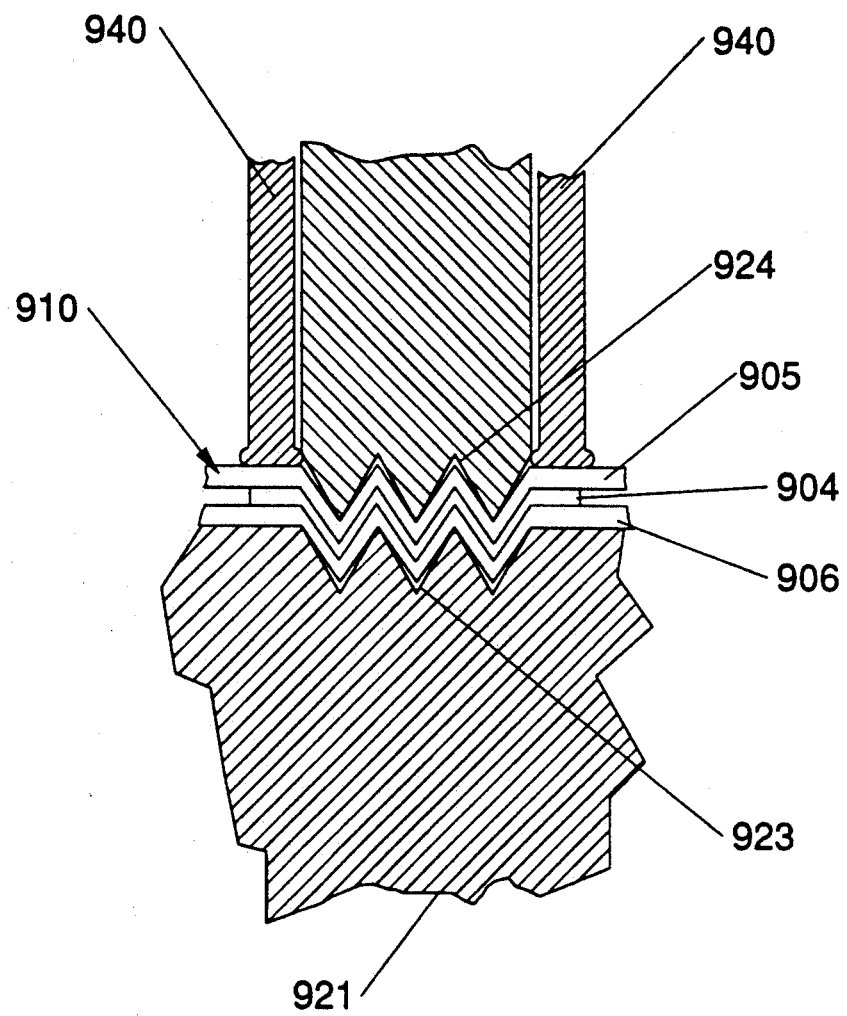
FIG. 9A is a highly enlarged simplified cross-sectional view taken at inset 9A shown in FIG. 9 along a centerline connection the uppermost corrugated rolls and the lower most corrugated rolls.

FIG. 9 discloses an alternative incremental web stretching system which can be employed. In the incremental web stretching system shown in FIG. 9, a pair of resiliently compressible disks 940 are mounted adjacent each side of the grooved segments 924 of the uppermost corrugated rolls 925. The compressible disks 940 are of a large enough diameter that they tightly grip the chassis web 910 and hold it securely against the coinciding non-grooved portions of the lowermost corrugated rolls 921 as generally shown in the cross-section of FIG. 9A. Like the vacuum ports and the porous honeycomb material in the embodiment of FIG. 8, the clamping effect created by the compressible disks 940 and the coinciding non-grooved portions of the lowermost rolls 921 substantially prevents the portion of the chassis web 910 containing the elastomeric patches 904 from contracting in a direction parallel to the direction of stretching as the web passes between the meshing corrugated rolls. The FIG. 9 embodiment can be used with equal facility on laminate structures comprised of webs which are either pervious or impervious to the passage of air.

As will be appreciated by those skilled in the art, the foregoing restraint methods may be employed either individually or in combination with one another to produce the benefits herein described in the resultant "zero strain" stretch laminate portions of the resultant chassis web.

From the description contained herein, it is clear that the improved method and apparatus may be employed to advantage to produce a wide range of disposable garments either comprised entirely of or including one or more discrete, isolated "zero strain" stretch laminate web portions.

It is also recognized that while a pair of meshing corrugated rolls having their corrugations aligned substantially parallel to one another are disclosed in the accompanying drawings, the present invention may be practiced with equal facility employing pairs of corrugated rolls wherein the corrugations are not all oriented parallel to one another. Furthermore, the corrugations on such pairs of corrugated rolls need not necessarily be aligned parallel to either the machine or the cross-machine direction. For example, if a curvilinear waistband or legband portion is desired in a disposable garment constructed using the "zero strain" stretch laminate technology herein disclosed, the meshing teeth on the pairs of corrugated rolls employed to incrementally stretch the "zero strain" laminate web portions of the chassis web may be arrayed in the desired curvilinear configuration to produce elasticity along the desired curvilinear contour rather than in a straight line.

It is further recognized that while the preferred processes herein disclosed employ meshing cylindrical corrugated rolls, the web restraint principles may also be carried out utilizing an intermittent stamping operation employing meshing platens to incrementally stretch the "zero strain" stretch laminate portions of the web or article in question. In the latter instance, the only requirement is that the portions of the "zero strain" stretch laminate web to be incrementally stretched be adequately restrained by suitable vacuum or clamping means before the meshing platens are able to exert enough force on the web to cause slippage or contraction in a direction parallel to the direction of stretching.

The elastic ear flap members 90 can be joined to either the inner layer 46, outer layer 48, or both using either an intermittent bonding configuration or a substantially continuous bonding configuration. As used herein, an "intermittently" bonded laminate web means a laminate web wherein the plies are initially bonded to one another at discrete spaced apart points or a laminate web wherein the plies are substantially unbonded to one another in discrete spaced apart areas. Conversely, a "substantially continuously" bonded laminate web means a laminate web wherein the plies are initially bonded substantially continuously to one another throughout the areas of interface. The intermittent bonding configuration is normally desirable for "zero strain" laminate webs in those situations where the substantially inelastic webs in the laminate are relatively elongatable or drawable without rupture and where a high degree of z-direction bulking is desired in the finished laminate. A continuous bonding configuration has generally been found desirable for "zero strain" laminate webs where the degree of z-direction bulking of the finished laminate is not of prime importance and one or more of the relatively inelastic webs in the laminate is difficult to elongate or draw without causing rupture. In the latter situation, a substantially continuous bonding configuration maintains all of the layers of the laminate in relatively close adherence to one another after the incremental stretching operation. Accordingly, even if one or more of the relatively inelastic webs is damaged to the point of rupture during the incremental stretching operation, the relatively close adherence of the damaged portions of the relatively inelastic web or webs to the elastomeric ply makes it difficult for the end user to perceive that any damage has occurred. Provided that the rupture of the relatively inelastic web or webs does not defeat the web's intended functionality, (e.g., imperviousness), the damage which does occur to the relatively inelastic web or webs during the incremental stretching operation is generally not perceived as a negative in the end product.

Thus, an unexpected benefit which results from the use of a continuous bonding configuration in particularly preferred "zero strain" stretch laminate webs is that it permits the manufacturer of the disposable garment to select from a much wider range of relatively inelastic webs which may be successfully employed in laminates of the present invention. In essence, it permits the use of relatively inelastic webs which would not normally be considered drawable to any appreciable extent in "zero strain" stretch laminate webs of the present invention. Accordingly, unless expressly stated otherwise, the term "drawable" as used herein, is not intended to exclude relatively inelastic webs which undergo a degree of thinning or damage during the incremental stretching operation.

In a preferred embodiment of the present invention, the elastic ear flap member 90 is substantially continuously bonded to both the inner layer 46 and the outer layer 48 using an adhesive. A glue applicator may be used to apply a substantially uniform and continuous layer of adhesive to the outer layer 48 and/or the inner layer 46 in those predetermined areas where the substantially untensioned elastic ear flap member 90 will be placed. In a particularly preferred embodiment, the adhesive selected is stretchable and the glue applicator comprises a melt blown applicating system.

One such melt blown adhesive applicating system which has been found to be particularly well suited for producing a substantially continuously bonded "zero strain" stretch laminate web is a melt blown spray applicator Model No. GM-50-2-1-GH, as available from J&M Laboratories of Gainesville, Ga. The latter system employs a nozzle having 20 orifices per lineal inch, as measured in the cross-machine direction, each orifice measuring approximately 0.020 inches in diameter. A Findley H-2247 Hot Melt Adhesive, as available from Findley Adhesives of Elm Grove, Wisc. is preferably heated to a temperature of approximately 340° F. and applied to the inner layer and/or the outer layer at a rate of approximately 7.5-10 milligrams per square inch. Heated compressed air at a temperature of issued through the secondary orifices in the adhesive nozzle to assist in uniformly distributing the adhesive fibrils during the laydown operation.

Alternatively, the elastic ear flap member 90 and any other components comprising the "zero strain" portions of the disposable training pants 20 may be intermittently or continuously bonded to one another using unheated adhesive, heat bonding, pressure bonding, ultrasonic bonding, dynamic mechanical bonding, or any other method as is known in the art.

The elastic ear flap members 90 may take on a number of different sizes, shapes, configurations and materials. For example, the elasticized ear flaps 30 may be formed from one or a plurality of elastic ear flap members 90 operatively associated in each ear flap 72; the elastic ear flap members may have varying widths and lengths; or the elastic ear flap members may comprise relatively narrow strands of elastomeric material or a larger area elastomeric patch. One elastomeric material which has been found to be especially suitable for use as the elastic ear flap member 90 (especially for "zero strain" stretch laminates) is an elastomeric foam having an elongation to break of at least about 400% and an extension force of at least about 200 grams per inch of sample width at 50% extension of its unstrained length. Exemplary elastomeric foams which have been found suitable for use as an elastic ear flap member include: (a) crosslinked natural rubber foams preferably having a caliper of approximately 35 mils and a density of 13.3 pounds per cubic foot (0.214 g/cm$^3$), such as is available from Fulflex Inc. of Middletown, R.I.; or as available from Ludlow Composites Corporation of Fremont, Ohio; or (b) polyurethane foams having a caliper of approximately 80 mils and a density of approximately 2.06 pounds per cubic foot (0.033 g/cm$^3$) such as is available from Bridgestone of Yokohama, Japan and marketed under the tradename Bridgestone SG polyurethane foam; or as available from General Foam of Paramus, N.J. and marketed under the designation of Polyurethane Foam No. 40310. Other suitable elastomeric materials for use as the elastic ear flap members 90 include "live" synthetic or natural rubber, other synthetic or natural rubber foams, elastomeric films (including heat shrinkable elastomeric films), elastomeric scrim, elastomeric woven or nonwoven webs, elastomeric composites such as elastomeric nonwoven laminates, or the like.

As shown in FIG. 1, the elastic ear flap member 90 comprises a patch of elastomeric material (elastomeric patch) that preferably extends through the entire length of the ear flap 72 in the front and rear portions 56, 58. Thus, the elastic ear flap member 90 preferably extends from the end edge 64 of the chassis 14 inward to the leg edge 106 of the ear flap 72. The length and width of the elastic ear flap members 90 are dictated by the disposable garment's functional design. Thus, while the elastic ear flap member 90 preferably extends through the entire length of the ear flap 72, the elastic ear flap member 90 may extend through only a portion of the length of the ear flap 72.

It has been found that the extension characteristics including the extension forces, extension modulus, and available stretch (extension); and the contractive forces; elastic creep; elastic hysteresis; and rate of contraction of the elasticized ear flaps 30 are important considerations in the performance of both the elasticized ear flaps 30 and the disposable garment. The extension characteristics give the wearer the overall perceived "stretchiness" during use. An elasticized ear flap with a relatively high extension modulus can cause red marking on the wearer's skin while a relatively low extension modulus can cause sagging/slipping on the wearer. Elasticized ear flap having too little available stretch may not achieve a suitable level of body conformity and may contribute in making the disposable garment uncomfortable to wear and hard to apply. A disposable garment having elasticized ear flaps with very low contractive forces, or poor elastic creep or elastic hysteresis may not stay in place on the wearer and may tend to sag/slip on the wearer resulting in poor fit and containment.

For the elasticized ear flaps 30 of the present invention, it has been found that the extension characteristics of extension force and extension modulus are preferably within defined ranges. The extension force preferably is 50-300 grams per linear inch. It is preferred that these extension forces be generated at extensions between about 20% and about 300% extension.

Available stretch measures the maximum amount of material available in the elasticized ear flaps to reversibly stretch to conform to the wearer's body during wear. Thus, the amount of available stretch relates to the maximum amount of extension that is available to fit the garment to the wearer; in addition, the maximum amount of recoverable extension available for the garment to comply with wearer's body. The available stretch is calculated from the equation: ((maximum circumference of garment—circumference of wearer)÷circumference of wearer)×100. The minimum amount of available stretch required for a disposable garment application using elasticized ear flaps, is preferably an available stretch of at least about 35% for a "one-size-fits-all" garment which will fit children from about 22 pounds to about 38 pounds.

The amount of sustainable contractive force (tension) exerted by the elasticized ear flap on the wearer is an important property of the elasticized ear flap. An elasticized ear flap with insufficient contractive forces may result in the training pant slipping down after being worn and loaded. In contrast, excessive contractive forces may reduce the comfort for the wearer and produce pressure markings on the wearer's skin. Contractive force is measured as the force per unit width produced while relaxing an elastomeric composite at a particular extension. In preferred embodiments of the present invention, the contractive force of the elasticized ear flaps is preferably at least about 50 grams/inch at 10% extension (a 10% extension would require the sample to be stretched to 1.1 times its original length).

Typical elastomeric materials show a hysteresis loop of force in their stress-strain property. That is, for a given extension, the force (extension force) required to uniaxially extend the elastomeric material is greater than the force (contractive force) the elastomeric material exerts when it is allowed to contract from its pre-extended condition. The former curve can be referred to as the "load curve" and the latter curve can be referred to as the "unload curve". The "load" extension force (extension force) is felt by the wearer or parent when the elasticized ear flap is stretched to apply the garment to the wearer. The wearer more nearly "feels" the "unload" contractive forces (contractive forces) once the garment is on. Therefore, the hysteresis loss should not be so great that the contractive force is low enough to allow sagging/slipping of the garment on the wearer.

All elastomeric materials undergoing sustained stress/strain have diminishing forces with time (i.e., elastic creep). Therefore, it is desired to make sure this reduction in wearing forces over time doesn't fall below a minimum for wearing stability. The elastic creep should therefore be kept at a minimum. In preferred embodiments of the present invention, the final length of the elastomeric material is not greater than about 1.2 times the original length under tension for 30 minutes.

The elasticized ear flaps 30 may also be provided with differential extensibility along the longitudinal axis when stretched in the lateral direction. As used herein, the term "differential extensibility" is used to mean a material having a nonuniform degree of elastic extensional properties, as measured in the direction of stretching at various points along an axis oriented substantially perpendicular to the direction of stretching. This may, for example, include varying the elastic modulus or available stretch or both of the elastomeric material(s). The differential extensibility is preferably designed into the elasticized ear flaps 30 so that the lateral extensibility varies longitudinally through at least a portion of the elasticized ear flap as measured from the end edge 64 of the disposable training pants 20 to the leg edge 106 of the ear flap. Without wishing to be bound by any theory, it is believed that differential extensibility along the longitudinal axis when stretched in the lateral direction allows the elasticized ear flap to differentially stretch and conform to the wearer's waist during use while providing a secure anchor about the hip of the wearer so as to promote sustained fit and reduce leakage at the waist and legs. Such a configuration may allow more "expansion" in the hip area to accommodate changes in the wearer's body size as the wearer moves and changes positions (standing, sitting, lying). In an alternative embodiment, a degree of reduced lateral extensibility in the portion of the elasticized ear flap adjacent to the end edge 64 of the disposable training pants 20 requires more of the total extension to be assumed by the elasticized waistband 34 thereby resulting in more localized stretching of the elasticized waistband 34 and a more compliant abdominal fit.

The differential extensibility can be achieved in a number of different ways. The elasticized ear flaps 30 can have multiple combined elastomeric materials, multiple configurations for the elastomeric materials, or the extension properties of the elastomeric or other material or materials making up the elasticized ear flap may be nonuniform. For example, differential extensibility can be achieved in selected adjacent portions of the elasticized ear flap by using elastomeric materials having varying extension or contractive forces, modulus, or other inherent properties such that more or less (varying) lateral extensibility is achieved in one portion of the elasticized ear flap than the adjacent portion. The elastomeric materials may also have varying lengths, sizes, and shapes that provide differential extensibility. Other ways of varying the properties of materials that form the elasticized ear flaps as are known in the art may also be used.

A particularly preferred method and apparatus for imparting a varying degree of extensibility to a "zero strain" stretch laminate is to pass the "zero strain" stretch laminate through at least one set of meshing corrugated rolls, at least one of the corrugated rolls having corrugations of nonuniform profile along its point or points of contact with the "zero strain" stretch laminate web. As a result, the portions of the laminate web passing between the set of rolls are nonuniformly stretched. This, in turn, produces a "zero strain" stretch laminate which is nonuniformly elasticized in a direction substantially perpendicular to the nonuniformly profiled corrugations.

In a preferred embodiment of the chassis as shown in FIG. 2, the longitudinal side region 88 is that portion of the chassis 14 that extends laterally outwardly from the ear flap 72 to the longitudinal edge 62 of the chassis 14. The longitudinal side region 88 generally extends longitudinally from the end edge 64 of the chassis 14 to the portion of the longitudinal edge 62 of the chassis 14 that forms the leg opening (this segment of the longitudinal edge 62 being designated as leg edge 106). While the longitudinal side region 88 can comprise a separate element affixed to the ear flap 72 of the chassis 14, the longitudinal side region is preferably an extension of other elements of the chassis 14 such as the inner layer 46, the outer layer 48, the topsheet 24 or the backsheet 26 or any combination of these elements. In a preferred embodiment of the present invention each longitudinal side region 88 is formed by portions of the inner layer 46 and outer layer 48 that extend beyond the ear flap 72.

Referring again to FIG. 1, seams 10 are preferably formed by bonding together the longitudinal side regions 88 of the front portion 56 with the longitudinal side regions 88 of the rear portion 58. The seam 10 can be formed in a number of different ways. For example, the seam 10 can be formed by bonding together portions of outwardly extending longitudinal side regions 88 to form an outwardly extending fin seam, bonding together portions of inwardly extending longitudinal side regions 88 to form an inwardly extending fin seam, the longitudinal side regions 88 may be overlapped and bonded together, or the longitudinal side regions 88 may be bonded together using any other seam configurations that are well known in the art. The bonding can be by any suitable means well known in the art appropriate for the specific material employed in the longitudinal side region 88 of the chassis 14; thus sonic sealing, heat sealing, adhesive bonding, sewing, and the like may be appropriate techniques. Examples of such seaming techniques are disclosed in U.S. Pat. No. 4,355,425 issued to Jones, et al. on Oct. 26, 1982; U.S. Pat. No. 4,619,649 issued to Roberts on Oct. 28, 1986; and U.S. Pat. No. 4,909,804 issued to Douglas, Sr. on Mar. 20, 1990.

Figure 5:
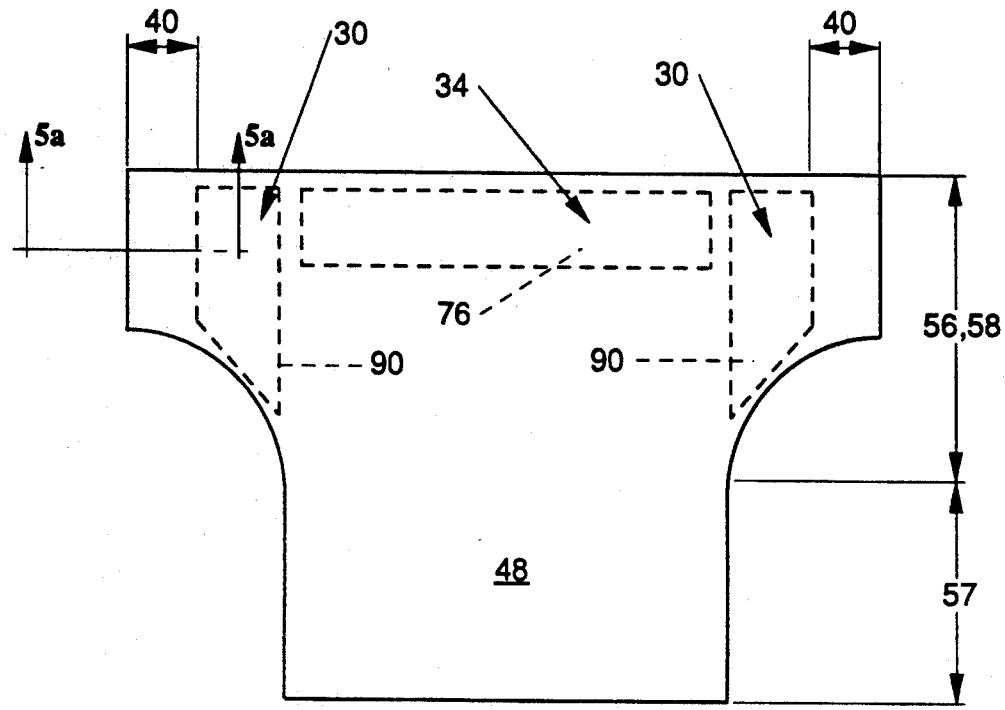
FIG. 5 is a plan view of the chassis of FIG. 2, having been folded in the crotch portion such that the front portion and rear portion are overlapped.
Figure 5A:
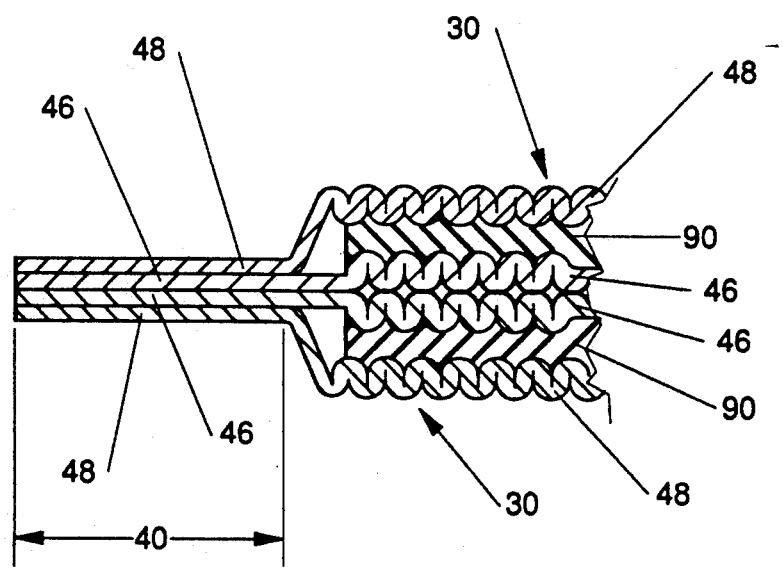
FIG. 5A is a fragmentary sectional view of the folded chassis shown in FIG. 5 taken along section line 5A—5A of FIG. 5.

In a preferred embodiment of the present invention, the disposable garment is formed by folding the chassis in the crotch portion 57 so that the longitudinal side regions 88 of the front portion 56 are substantially superposed with the longitudinal side regions 88 of the rear portion 58, as shown in FIG. 5, forming two seaming areas 40. FIG. 5A shows a preferred embodiment of the seaming area 40 comprising the longitudinal side region 88 of the front portion 56 and the longitudinal side region 88 of the rear portion 58. Preferably, the layers of material making-up the seaming area, have similar melting points. More preferably, each layer of the seaming area is made of the same material. In a preferred embodiment, each layer of the seaming area 40 will comprise 100% polypropylene fibers.

The seam 10 is preferably formed by treating the seaming area 40 with mechanical energy sufficient to cut a portion of the seaming area 40 while simultaneously fusing a narrow marginal area adjacent to the cut. The fused marginal area is a relatively small region and provides a finished flangeless seam. As used herein the term "flangeless seam" refers to a seam which extends from the disposable training pants 20 about 1/16" or less Preferably the flangeless seam will extend from the garment about 1/32" or less. In a preferred embodiment, the flangeless seam is substantially a splice between the front portion 56 and rear portion 58 of the chassis 14. As used herein, the term "splice" refers to the act or result of joining end to end two pieces of sheet material to form a continuous length such that the thickness of the joint is no greater or not much greater than the thickness of the sheet materials.

Although there is considerable evidence to indicate that all energy is mechanical energy, there are forms of energy which may be considered "non-mechanical" energy, such as thermal energy, electrical energy, and chemical energy. However, as used herein, the term "mechanical energy" will be used to refer to mechanical energy (e.g., the energy employed in ultrasonic bonding or autogeneous pressure bonding) as well as to thermal energy (e.g., the energy employed in heat sealing). Preferably, ultrasonic energy is used to simultaneously cut and bond the seaming area 40 to produce the seams 10 of the present invention.

Preferably, the mechanical energy is input to the seaming area 40 using an ultrasonic apparatus. An ultrasonic apparatus will generally comprise an ultrasonic converter unit which receives high frequency electrical energy from an electrical energy source via an electrical conductor. The converter unit contains piezoelectric transducer material for providing, in response to high frequency input power, mechanical vibrations to a horn which will oscillate back and forth relative to a support surface which acts as an anvil.

Figure 6:
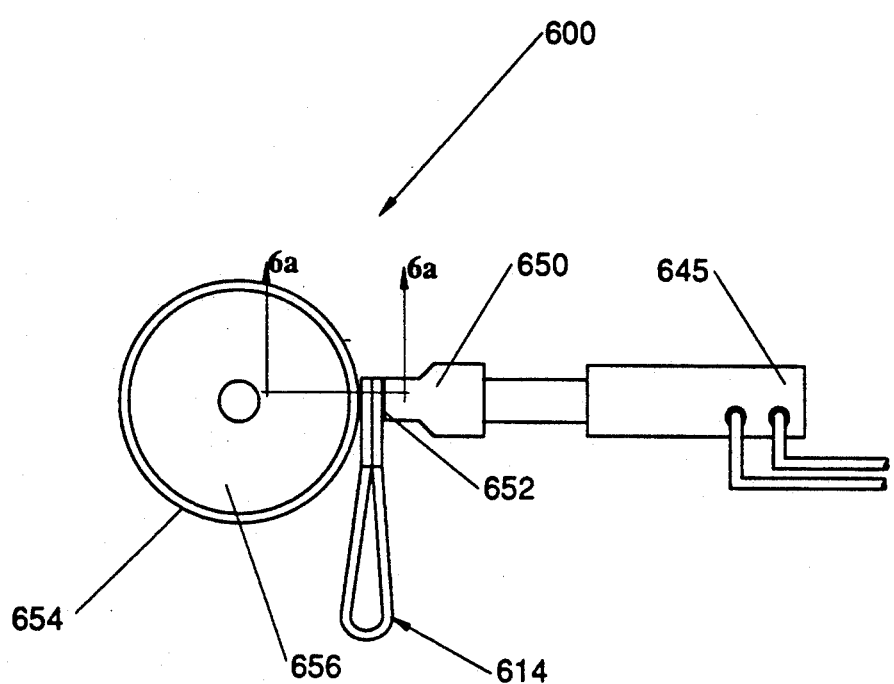
FIG. 6 is a side elevational schematic view of one ultrasonic apparatus which may be used to produce the seams of the present invention.

FIG. 6 is a side elevational schematic view of a preferred ultrasonic apparatus, shown generally at 600. The ultrasonic horn 650 having a working tip 652 is coupled to an ultrasonic converter unit 645 which receives high frequency electrical energy from an electrical energy source (not shown). The working tip 652 of the horn 650 is opposed by an anvil 654 mounted on an axially rotatable roll 656. The folded chassis 614 of the disposable garment is shown passing between the working tip 652 and anvil 654. The ultrasonic horn 650 is operated at an ultrasonic frequency preferably in the range of about 20 kHz to about 40 kHz, but any other frequency in the normal operating range between 16 and 100 kHz will be suitable.

Figure 6A:
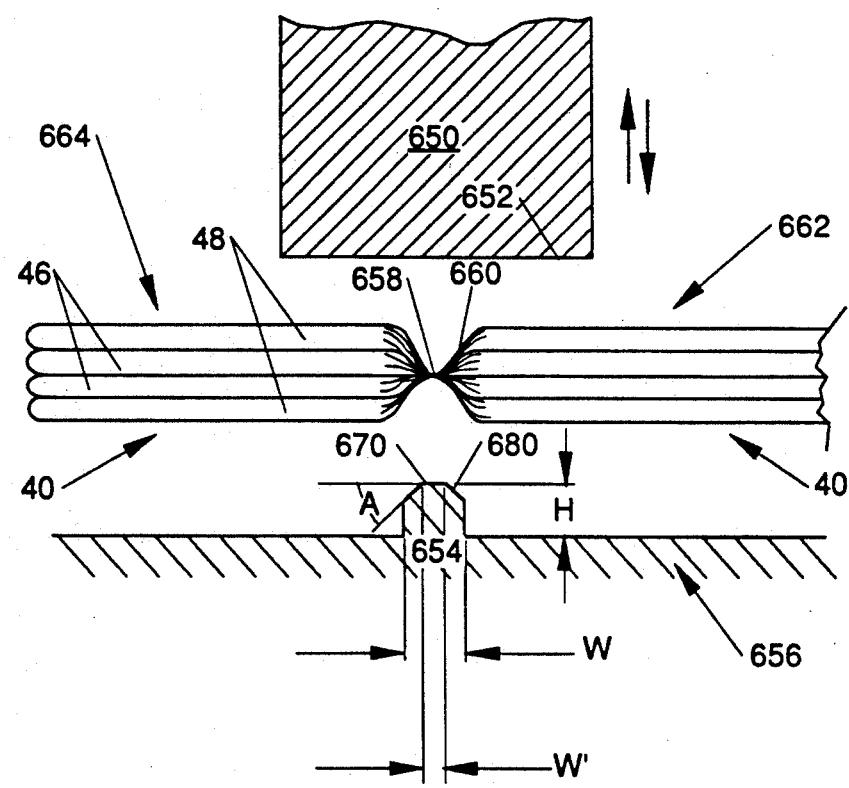
FIG. 6A is a fragmentary sectional view of the apparatus shown in FIG. 6 taken along section line 6A—6A of FIG. 6.

FIG. 6A shows a cross-sectional view of the seaming apparatus 600 of FIG. 6. The seaming area 40 of the folded chassis 614 is shown passing between the anvil 654 and the working tip 652, as the horn 650 oscillates back and forth, i.e. toward and away from the anvil 654. The ultrasonic energy of the seaming apparatus 600 causes the layers of polymeric material of the seaming area 40 to soften and flow, thinning or cutting the seaming area 40 in a first area 658 while fusing the seaming area 40 in the thin marginal areas adjacent the first area 658 forming a fused mass 660. While the portion 664 of the seaming area 40 which has been cut away from the disposable training pants 20, will be disposed as selvage, the fused mass 660 of the portion 662 of the seaming area 40 which is still part of the disposable training pants 20 will provide to the disposable training pants 20 a finished seam 10 which is substantially a splice between the front portion 56 and rear portion 58.

The anvil 654 of the preferred seaming apparatus 600 shown in FIG. 6A, has a contacting edge 670. The width of the contacting edge is designated by the letter W, and is preferably about 0.0.030 inches. The anvil 654 also has beveled edges 680 which form an angle with the contacting edge 670. The angle of the beveled edges is designated by the letter A and is preferably about 15°. The width of the anvil 654 is designated by the letter W and is preferably about 0.100 inches. The height of the anvil is designated by the letter H and is preferably about 0.100 inches.

Without being bound by any particular theory, it is believed that the ultrasonic horn 650 creates, by virtue of its high speed low amplitude oscillations, localized frictional losses, the heat of which causes the polymeric fibers of the seaming area 40 to soften and to fuse. This welding or fusing action is very rapid and occurs within such a well defined zone as to leave the surrounding material substantially undisturbed.

Examples of methods and apparatus for treating materials with ultrasonic energy are disclosed in U.S. Pat. No. 3,657,033 issued to Sager on Apr. 18, 1972 entitled "Method and Apparatus for Continuous Cutting and Joining of Thermoplastic Sheet Material"; U.S. Pat. No. 4,400,227 issued to Riemersma on Aug. 23, 1983; U.S. Pat. No. 4,430,148 issued to Schaefer on Feb. 7, 1984; U.S. Pat. No. 4,560,427 issued to Flood on Dec. 24, 1985 entitled "Ultrasonic Seal and Cut Method and Apparatus"; and U.S. Pat. No. 4,693,771 issued to Payet, et al. on Sep. 15, 1987 entitled "Woven Textile Fabric Having and Ultrasonically Cut and Sealed Edge and Apparatus and Process for Producing Same"; all of which references are incorporated herein by reference. U.S. Pat. No. 3,457,132 issued to Tuma, et al. on Jul. 22, 1969 entitled "Apparatus for Severing and Sealing Webs of Heat Sealable Packaging Material in a Single Operation", discloses a method and apparatus for severing and sealing webs of heat sealable material using thermal energy. This reference is also incorporated herein by reference.

The present inventors have found that when making the small flangeless seams of the present invention, it is preferable that the layers of polymeric material of the seaming area 40, have similar melting points. It is more preferable that the seaming area 40 be made of layers of the same polymeric material. In a preferred embodiment, each layer of the seaming area 40 will be a nonwoven comprising 100% polypropylene fibers.

Figure 7:
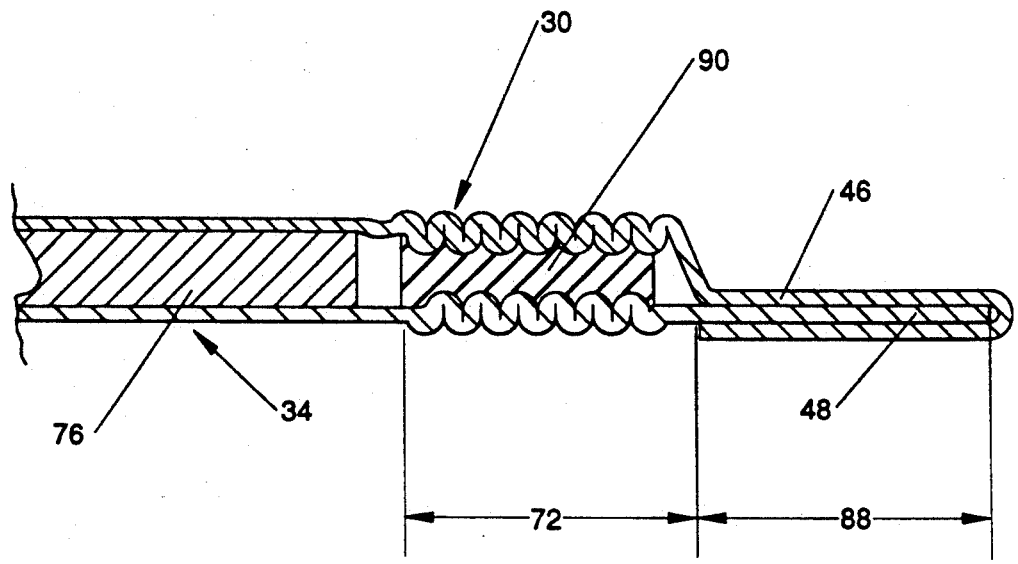
FIGS. 7 & 7A are fragmentary sectional views of the longitudinal side region of alternate embodiments of the present invention.
Figure 7A:
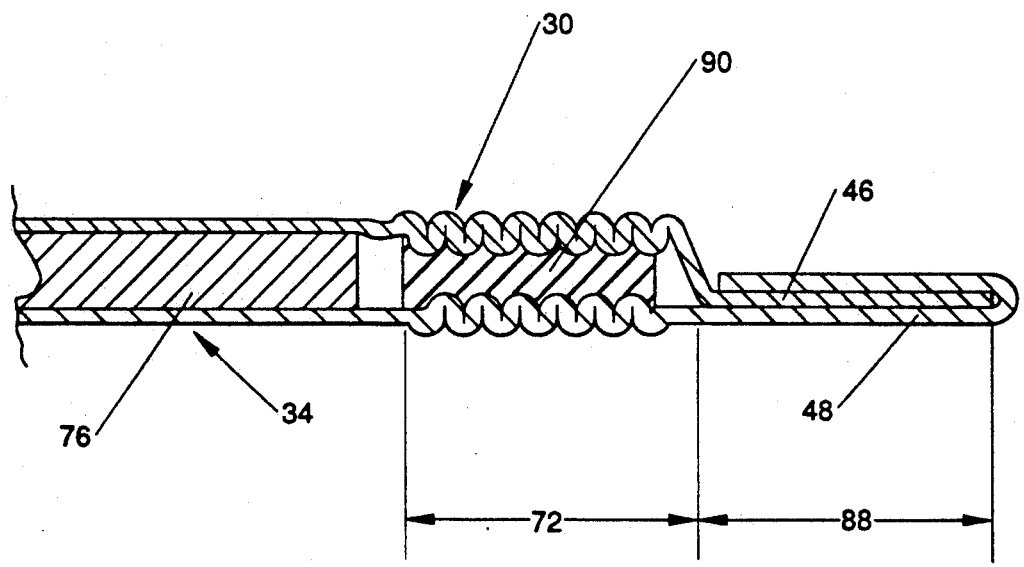

The strength of the flangeless seams of the present invention can be increased by using polymeric material having a higher basis weight. If the material of the longitudinal side regions 88 is very thin, the seaming area 40 may not contain sufficient material to form an adequate seam, e.g. the seam may not be strong enough for the garment. In this situation, additional layers of material may be introduced to the longitudinal side region 88 such that the seaming area 40 will contain sufficient material to form an adequate seam. Embodiments of the present invention which provide additional layers of material in the longitudinal side regions 88 and therefore provide additional material to the seaming area 40, are shown in the fragmentary sectional views of FIGS. 7 and 7A. FIG. 7 shows the inner layer 46 being folded over the outer layer 48 in the longitudinal side region 88 to provide three layers of material in the longitudinal side region 88. FIG. 7A shows the outer layer 48 being folded over the inner layer 46 in the longitudinal side region 88 to provide three layers of material in the longitudinal side region 88.

Figure 11:
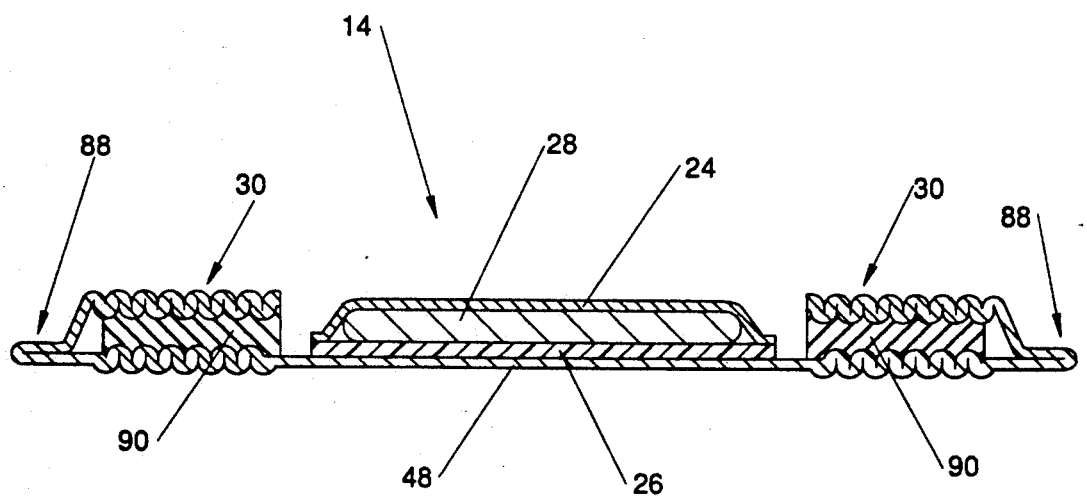
FIG. 11 is a sectional view of the chassis of an alternate embodiment of the present invention.

FIG. 11 shows an alternative embodiment of the present invention wherein the chassis 14 comprises an outer layer 48 which is folded to envelope the elastic ear flap members 90 and formed the longitudinal side regions 88. The absorbent assembly 22 is secured to the outer layer 48 and comprises a topsheet 24, backsheet 26 and absorbent core 28.

The training pants 20 will also comprise an absorbent assembly 22. The absorbent assembly 22 of the disposable training pants 20 is an insert, i.e. an element formed separately from the chassis and inserted therein. The absorbent assembly 22 is any absorbent means which is generally compressible, conformable, non-irritating to the wearer's skin, and capable of absorbing and retaining liquids such as urine and other certain body exudates.

As shown in FIG. 2, the absorbent assembly 22 of the disposable training pants 20 preferably comprises an absorbent core 28 and an outer covering layer comprising a topsheet 24 and a backsheet 26. The absorbent assembly 22 is preferably positioned adjacent the inner layer 46 and is preferably joined thereto by attachment means (not shown) such as those well known in the art. Suitable attachment means are described hereinbelow with respect to joining the backsheet 26 to the absorbent core 28.

Figure 4:
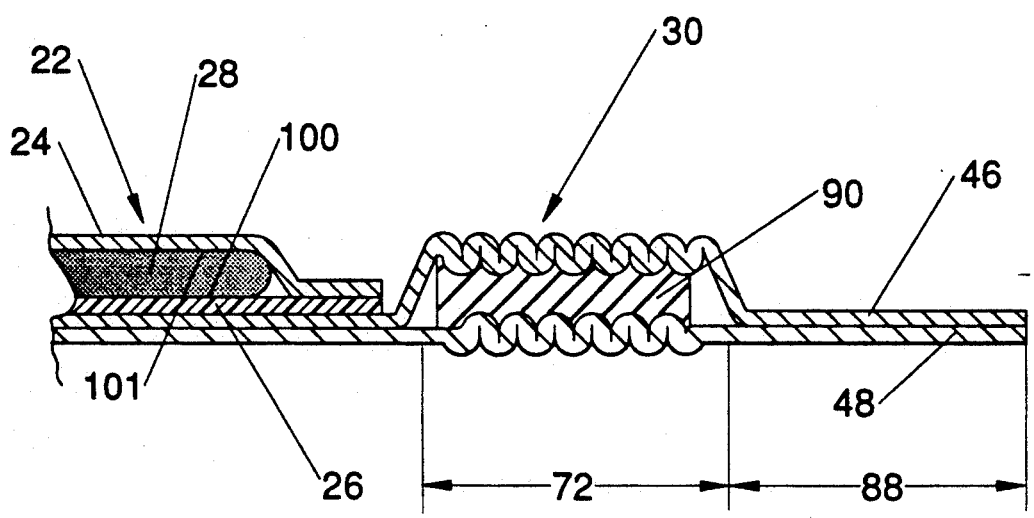
FIG. 4 is a fragmentary sectional view of the chassis shown in FIG. 2 taken along section line 4—4 of FIG. 2.

The absorbent core 28 may be any absorbent means which is generally compressible, conformable, non-irritating to the wearer's skin, and capable of absorbing and retaining liquids such as urine and other certain body exudates. As shown in FIG. 2 and FIG. 4, the absorbent core 28 has a garment surface 100, a body surface 101, side edges 82 and end edges 83.

The absorbent core 28 may be manufactured in a wide variety of sizes and shapes (e.g., rectangular, hourglass, "T"-shaped, asymmetric, etc.) and from a wide variety of liquid-absorbent materials commonly used in disposable diapers and other absorbent articles such as comminuted wood pulp which is generally referred to as airfelt. Examples of other suitable absorbent materials include creped cellulose wadding, meltblown polymers including coform, cross-linked cellulosic fibers, tissue including tissue wraps, absorbent foams, absorbent sponges, superabsorbent polymers, absorbent gelling materials, or any equivalent material or combinations of materials. The configuration and construction of the absorbent core may also be varied (e.g., the absorbent core may have varying caliper zones, a hydrophilic gradient, a superabsorbent gradient, or lower average density and lower average basis weight acquisition zones; or may comprise one or more layers or structures). The total absorbent capacity of the absorbent core 28 should, however, be compatible with he design loading and the intended use of the disposable training pants 20. Further, the size and absorbent capacity of the absorbent core 28 may be varied to accommodate wearers ranging from infants through adults.

A preferred embodiment of the absorbent assembly 22 has a symmetric, modified hour-glass shape absorbent core 28. While a preferred embodiment of the absorbent assembly 22 has a modified hourglass-shaped absorbent core 28, it should be understood that the size, shape, configuration and total absorbent capacity of the absorbent core 28 may be varied to accommodate wearers ranging from infants to adults. Therefore, the dimensions, shape and configuration of the absorbent core may be varied (e.g., the absorbent core may have a varying caliper, or a hydrophilic radiant, or may or may not contain absorbent gelling materials). An exemplary absorbent structure for use as the absorbent core 28 of the present invention that has achieved wide acceptance and commercial success is described in U.S. Pat. No. 4,610,678 entitled "High-Density Absorbent Structures" issued to Weisman and Goldman on Sep. 9, 1986. U.S. Pat. No. 4,673,402 entitled "Absorbent Articles With Dual-Layered Cores" issued to Weisman, Houghton, and Gellert on Jun. 16, 1987; U.S. Pat. No. 4,834,735 entitled "High Density Absorbent Members Having Lower Density and Lower Basis Weight Acquisition Zones" issued to Alemany and Berg on May 30, 1989; and U.S. Pat. No. 4,888,231 entitled "Absorbent Core Having A Dusting Layer" issued to Angstadt on Dec. 19, 1989; also describe absorbent structures that are useful in the present invention. Each of these references are incorporated herein by reference. The absorbent core 28 is preferably a batt of airfelt and particles of absorbent gelling material, about 13 centimeters wide (lateral dimension), about 37 centimeters long (longitudinal dimension) and approximately 8 centimeters across the narrowest part of the crotch portion 57. Preferably, the portion of the absorbent core that will be generally located in the front portion 56 and crotch portion 57 will have a higher basis weight than the portion of the absorbent core that will be generally located in the rear portion 58. More preferably, the portion of the absorbent core that will be generally located in the front portion 56 and crotch portion 57 will have a basis weight three times the basis weight of the portion of the absorbent core that will be generally located in the rear portion 58. In a preferred embodiment of the absorbent core 28, about 25.4 centimeters of the absorbent core's length will be generally located in the front portion 56 and crotch portion 57 and will have a basis weight of about 0.69 grams per square inch, and 11.4 centimeters of the absorbent core's length will be generally located in the rear portion 58 and will have a basis weight of about 0.23 grams per square inch.

The backsheet 26 is positioned adjacent the garment surface 100 of the absorbent core 28 and is preferably joined thereto by attachment means (not shown) such as those well known in the art. For example, the backsheet 26 may be secured to the absorbent core 28 by a uniform continuous layer of adhesive, a patterned layer of adhesive, or an array of separate lines, spirals, or spots of adhesive. Adhesives which have been found to be satisfactory are manufactured by Century Adhesives, Inc. of Columbus, Ohio and marketed as Century 5227; and by H. B. Fuller Company of St. Paul, Minn. and marketed as HL-1258. The attachment means will preferably comprise an open pattern network of filaments of adhesive as is disclosed in U.S. Pat. No. 4,573,986 entitled "Disposable Waste-Containment Garment", which issued to Minetola and Tucker on Mar. 4, 1986, and which is incorporated herein by reference. An exemplary attachment means of an open pattern network of filaments comprises several lines of adhesive filaments swirled into a spiral pattern such as is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

The backsheet 26 is impervious to liquids (e.g., urine) and is preferably manufactured from a thin plastic film, although other flexible liquid impervious materials may also be used. As used herein, the term "flexible" refers to materials which are compliant and will readily conform to the general shape and contours of the human body. The backsheet 26 prevents the exudates absorbed and contained in the absorbent core 28 from wetting articles which contact the disposable training pants 20 such as bedsheets and undergarments. The backsheet 26 may thus comprise a woven or nonwoven material, polymeric films such as thermoplastic films of polyethylene or polypropylene, or composite materials such as a film-coated nonwoven material. Preferably, the backsheet is a film having a thickness of from about 0.012 mm (0.5 mil) to about 0.051 mm (2.0 mils).

The size of the backsheet 26 is dictated by the size of the absorbent core 28 and the exact disposable garment design selected. In a preferred embodiment, the backsheet 26 will wrap around at least the absorbent core and possibly over the edge portions of the topsheet 24 in at least the crotch portion 57, so that the elasticized leg cuff 32 will be free from any backsheet material, and, thus, are not inhibited by the backsheet material. Alternatively, the topsheet 24 may wrap around the core and under the edge portions of the backsheet 26 in at least the crotch portion 57, or the topsheet 24 and backsheet 26 may be "side-notched" in the crotch portion 57 so that the elasticized leg cuffs 32 are not inhibited by the backsheet material.

The topsheet 24 is positioned adjacent the body surface 101 of the absorbent core 28 and is preferably joined thereto and to the backsheet 26 by attachment means (not shown) such as those well known in the art. Suitable attachment means are described with respect to joining the backsheet 26 to the absorbent core 28. In a preferred embodiment of the present invention, the topsheet 24 and the backsheet 26 are joined directly to each other in the areas extending beyond the absorbent core 28 and are indirectly joined together by directly joining them to the absorbent core 28 by the attachment means (not shown).

The topsheet 24 is compliant, soft feeling, and non-irritating to the wearer's skin. Further, the topsheet 24 is liquid pervious permitting liquids (e.g., urine) to readily penetrate through its thickness. A suitable topsheet may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. Preferably, the topsheet 24 is made of hydrophilic material comprising about 20% to 30% rayon so as to feel wet and signal a discharge of urine to a toilet training child.

There are a number of manufacturing techniques which may be used to manufacture the topsheet 24. For example, the topsheet 24 may be a nonwoven web of fibers. When the topsheet comprises a nonwoven web, the web may be spunbonded, carded, wet-laid, melt-blown, hydroentangled, combinations of the above, or the like. A preferred topsheet is carded and thermally bonded by means well known to those skilled in the fabrics art. A suitable topsheet is manufactured by Fiberweb North America and available as 80/20 polypropylene/rayon carded thermally bonded nonwoven.

Figure 10:
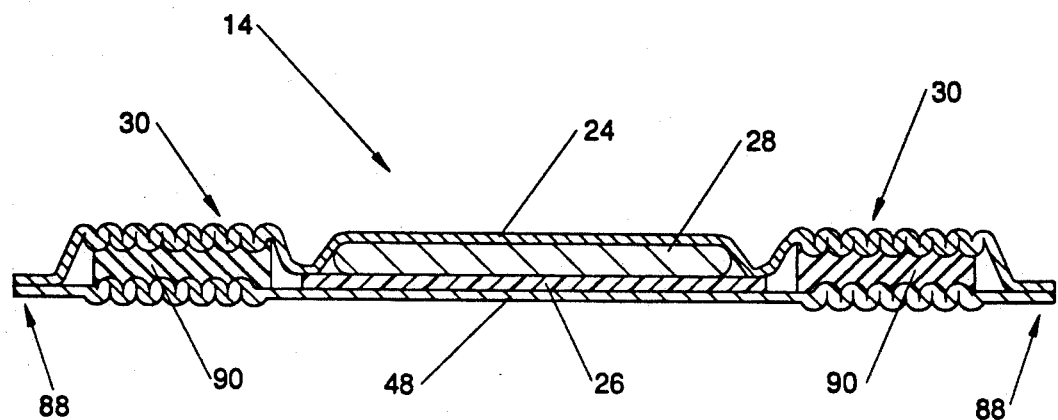
FIG. 10 is a sectional view of the chassis of an alternate embodiment of the present invention.

While in a preferred embodiment of the present invention, the topsheet 24 does not form a part of the chassis 14, but is separately manufactured and inserted as part of the absorbent assembly 22 onto the chassis, the chassis 14 may be made without an inner layer 46, and the topsheet 24 of the absorbent assembly 22 may extend beyond the edges of the backsheet 26 in at least the front and rear portions 56, 58 of the chassis 14 such that the topsheet 24 will be disposed over the elastic ear flap members 90 and form the inner surface of the chassis 14 (shown in FIG. 10). In this embodiment, at least a portion of the topsheet 24 is subjected to mechanical stretching in order to provide a "zero strain" stretch laminate that forms the elasticized ear flaps 30. Thus, the topsheet 24 of this embodiment should be elongatable, preferably drawable, but not necessarily elastomeric, so that the topsheet 24 will, upon mechanical stretching, be at least to a degree permanently elongated such that it will not fully return to its original configuration. However, this embodiment is not preferred because urine may "wick" beyond the central region 68 of the chassis 14 and fail to be contained within the absorbent assembly 22.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An elasticized disposable garment comprising:
   (a) a chassis having:
      (i) a front portion having an end edge, longitudinal side edges, leg edges, a central region, ear flaps each said ear flap extending laterally outwardly from said central region to said longitudinal side edges and longitudinally along said central region from said end edge to said leg edge;
      (ii) a rear portion opposed to said front portion, said rear portion having an end edge, longitudinal side edges, leg edges, a central region, ear flaps each said ear flap extending laterally outwardly from said central region to said longitudinal side edges and longitudinally along said central region from said end edge to said leg edge; and
      (iii) a crotch portion between said front portion and said rear portion;
      said chassis comprising an outer layer, an elastic waistband member joined to said outer layer in at least said central region of said front portion to form an elasticized waistband, a second elastic waistband member joined to said outer layer in at least said central region of said rear portion to form a second elasticized waistband, and an elastic ear flap member joined to each said ear flap and extending longitudinally from said end edge of said ear flap toward said leg edge of said ear flap to form an elastomeric laminate, each said elastomeric laminate being mechanically stretched to form an elasticized ear flap in each said ear flap of said chassis, each said elasticized ear flap being unitary with said chassis in that said elasticized ear flap comprises a portion of said outer layer and
   (b) seams joining said front portion to said rear portion adjacent said longitudinal side edges so as to form two leg openings and a waist opening substantially encircled by said end edges.

2. The elasticized disposable garment of claim 1 wherein said chassis additionally comprises an inner layer secured to said outer layer.

3. The elasticized disposable garment of claim 2 wherein said elastic ear flap members are interposed between said outer layer and said inner layer of said chassis.

4. The elasticized disposable garment of claim 3 wherein said chassis additionally comprises an absorbent assembly secured to said inner layer.

5. The elasticized disposable garment of claim 4 wherein said absorbent assembly comprises a topsheet, a backsheet secured to said topsheet, and an absorbent core interposed between said topsheet and said backsheet, said backsheet being secured to said inner layer.

6. The elasticized disposable garment of claim 3 wherein said inner layer comprises a liquid pervious nonwoven material that forms a topsheet.

7. The elasticized disposable garment of claim 6 wherein said chassis additionally comprises an absorbent core interposed between said topsheet and said outer layer.

8. The elasticized disposable garment of claim 5 wherein said chassis further comprises an elasticized waistband disposed in at least said rear portion.

9. The elasticized disposable garment of claim 5 wherein said chassis further comprises elasticized leg cuffs disposed in at least said crotch region.

10. The elasticized disposable garment of claim 5 wherein said inner layer and said outer layer each comprise a 100% polymeric nonwoven material.

11. The elasticized disposable garment of claim 5 wherein said elastic ear flap member comprises a cross-linked natural rubber foam.

12. The elasticized disposable garment of claim 1, 3, 5, 7, or 11 wherein said seams each comprise a mass of fused polymeric material, which extend from the disposable garment about 1/16 of an inch or less.

13. The elasticized disposable garment of claim 12 wherein said seams each comprise a mass of fused polymeric material which forms a splice between said front portion and said rear portion.

* * * * *

UNITED STATES PATENT AND TRADEMARK OFFICE
CERTIFICATE OF CORRECTION

PATENT NO. : 5,246,433

DATED : September 21, 1993

INVENTOR(S) : MARGARET H. HASSE, et al.

It is certified that error appears in the above-identified patent and that said Letters Patent is hereby corrected as shown below:

Column 4, line 47, "Joined" should read --joined--.

Column 4, line 68, "Join-" should read --join-- --.

Column 6, line 14, "Joined" should read --joined--.

Column 11, line 3, "use" should read --user--.

Column 13, line 44, after the words "temperature of" insert --approximately 425°F and a pressure of approximately 50 psig is--.

Column 15, line 6, "wearer)-" should read --wearer)--.

Column 18, line 46, "W," should read --W'--.

Column 18, line 46 "0.0.030" should read --0.030--.

Column 20, line 29, "he" should read --the--.

Signed and Sealed this

Thirtieth Day of April, 1996

Attest:

BRUCE LEHMAN

Attesting Officer

Commissioner of Patents and Trademarks